US 6,706,530 B2

(12) United States Patent
Hillenkamp

(10) Patent No.: US 6,706,530 B2
(45) Date of Patent: *Mar. 16, 2004

(54) IR-MALDI MASS SPECTROMETRY OF NUCLEIC ACIDS USING LIQUID MATRICES

(75) Inventor: Franz Hillenkamp, Muenster (DE)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/309,125

(22) Filed: May 10, 1999

(65) Prior Publication Data

US 2003/0148528 A1 Aug. 7, 2003

Related U.S. Application Data

(63) Continuation of application No. 09/074,936, filed on May 7, 1998.

(51) Int. Cl.[7] .................. G01N 33/50; G01N 33/48; G01N 27/64; B01D 59/44; H01J 49/00
(52) U.S. Cl. ............... 436/94; 436/43; 436/86; 436/91; 436/93; 436/173; 436/174; 436/181
(58) Field of Search ............... 436/43, 91, 86, 436/93–94, 173–174, 181

(56) References Cited

U.S. PATENT DOCUMENTS

| 3,568,735 A | 3/1971 | Lancsaster ............... 141/238 |
| 3,776,700 A | 12/1973 | Gallant ................... 422/65 |
| 3,807,235 A | 4/1974 | Lefkovitz ................ 73/863.32 |
| 3,999,689 A | 12/1976 | Ciantro et al. ............ 222/108 |
| 4,139,346 A | 2/1979 | Rabbani ................... 422/56 |
| 4,214,159 A | 7/1980 | Hillenkamp et al. ........ 250/288 |
| 4,442,354 A | 4/1984 | Hurst et al. .............. 250/281 |
| 4,461,328 A | 7/1984 | Kenney ................... 422/100 |

(List continued on next page.)

FOREIGN PATENT DOCUMENTS

| DE | 3221681 | 12/1983 |
| DE | 3930312 | 4/1990 |
| DE | 4011991 | 10/1990 |
| EP | 0268237 | 5/1988 |
| EP | 0269520 | 6/1988 |
| EP | 0339781 | 11/1989 |
| EP | 0360677 | 3/1990 |
| EP | 0396116 | 11/1990 |

(List continued on next page.)

OTHER PUBLICATIONS

Eperon, I. C., Rapid preparation of bacteriophage DNA for sequence analysis in sets of 96 clones, using filtration, *Anal. Biochem* 156:406–412 (1986).
Hopert et al., Specifity and sensitivity of polymerase chain reaction (PCR) in comparison with other methods for the detection of mycoplasma contamination in cell lines, *J. Immunol. Methods* 164:91–100 (1993).
Köster et al., Some improvements in the synthesis of DNA of biological interest, *Nucl Acids Res* 7:39–59 (1980).
Köster et al., Well–defined insoluble primers for the enzymatic synthesis of oligo– and polynucleotides, *Hoppe–Seyler's Z. Physiol. Chem.* 359:11579–1589 (1978).
Matthews, et al., "Analytical strategies for the use of DNA probes", *Analytical Biochemistry* 169:1–25 (1988).
Melton et al., Efficient in vitro synthesis of biologically active RNA and RNA hybridization probes from plasmids containing a bacteriophage SP6 promoter, *Nucl. Acids Res.* 12:7035–7056 (1984).

(List continued on next page.)

Primary Examiner—Arlen Soderquist
(74) Attorney, Agent, or Firm—Stephanie L. Seidman; Heller Ehrman White & McAuliffe, LLP

(57) ABSTRACT

Mass spectrometry of large nucleic acids by infrared Matrix-Assisted Laser Desorption/Ionization (MALDI) using a liquid matrix is reported.

22 Claims, 3 Drawing Sheets

U.S. PATENT DOCUMENTS

Figure 1A:
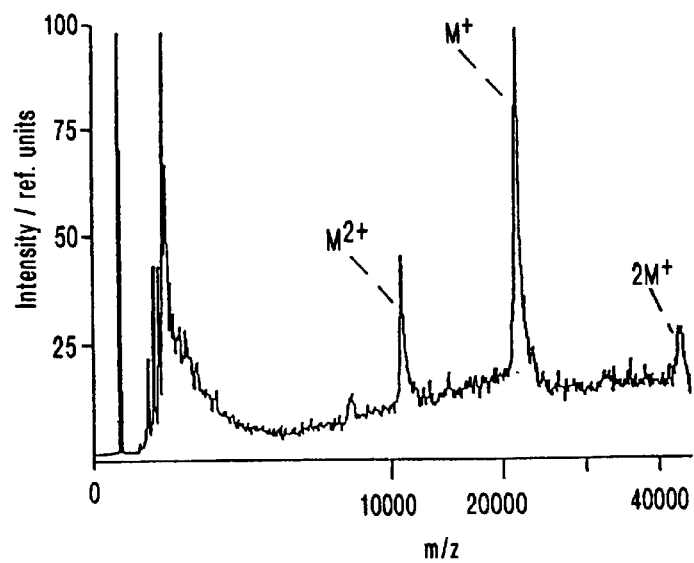

| | | | |
|---|---|---|---|
| 4,548,245 A | 10/1985 | Crandell et al. | 141/237 |
| 4,554,839 A | 11/1985 | Hewett et al. | 73/864.16 |
| 4,582,789 A | 4/1986 | Sheldon, III et al. | 435/6 |
| 4,683,194 A | 7/1987 | Saiki et al. | 435/6 |
| 4,683,195 A | 7/1987 | Mullis et al. | 435/6 |
| 4,725,677 A | 2/1988 | Köster et al. | 536/27 |
| 4,729,947 A | 3/1988 | Middendorf et al. | 435/6 |
| 4,731,335 A | 3/1988 | Brigati | 436/180 |
| 4,757,141 A | 7/1988 | Fung et al. | 536/27 |
| 4,778,993 A | 10/1988 | Waugh | 250/287 |
| 4,779,467 A | 10/1988 | Rainin et al. | 73/864.17 |
| 4,797,355 A | 1/1989 | Stabinsky | 435/6 |
| 4,798,706 A | 1/1989 | Brigati | 422/102 |
| 4,806,546 A | 2/1989 | Carrico et al. | 536/27 |
| 4,844,298 A | 7/1989 | Ohoka et al. | 222/58 |
| 4,855,225 A | 8/1989 | Fung et al. | 435/6 |
| 4,877,745 A | 10/1989 | Hayes et al. | 436/166 |
| 4,882,127 A | 11/1989 | Rosenthal et al. | 422/50 |
| 4,902,481 A | 2/1990 | Clark et al. | 422/101 |
| 4,920,264 A | 4/1990 | Becker | 250/282 |
| 4,925,629 A | 5/1990 | Schramm | 422/82.05 |
| 4,931,400 A | 6/1990 | Jitsukawa | 435/287 |
| 4,948,442 A | 8/1990 | Manns | 156/73.1 |
| 4,948,882 A | 8/1990 | Ruth | 536/27 |
| 4,952,518 A | 8/1990 | Johnson et al. | 436/518 |
| 4,983,521 A | 1/1991 | Lingappa et al. | 435/172.3 |
| 4,994,373 A | 2/1991 | Stavrianopoulos et al. | 435/6 |
| 5,000,921 A | 3/1991 | Hanaway et al. | 422/100 |
| 5,003,059 A | 3/1991 | Brennan | 536/27 |
| 5,023,187 A | 6/1991 | Koebler et al. | 436/180 |
| 5,045,694 A | 9/1991 | Beavis et al. | 250/287 |
| 5,047,215 A | 9/1991 | Manns | 422/101 |
| 5,062,935 A | 11/1991 | Schlag et al. | 204/157.41 |
| 5,064,754 A | 11/1991 | Mills | 435/6 |
| 5,077,210 A | 12/1991 | Eigler et al. | 435/176 |
| 5,082,935 A | 1/1992 | Cruickshank | 536/27 |
| 5,108,703 A | 4/1992 | Pfost et al. | 422/65 |
| 5,118,605 A | 6/1992 | Urdea | 435/6 |
| 5,118,937 A | 6/1992 | Hillenkamp et al. | 250/282 |
| 5,135,870 A | 8/1992 | Williams et al. | 436/86 |
| 5,149,625 A | 9/1992 | Church et al. | 435/6 |
| 5,160,840 A | 11/1992 | Vestal | 250/287 |
| 5,171,989 A | 12/1992 | Williams et al. | 250/288 |
| 5,195,657 A | 3/1993 | Wells | 222/330 |
| 5,202,561 A | 4/1993 | Giessmann et al. | 250/281 |
| 5,210,412 A | 5/1993 | Levis et al. | 250/288 |
| 5,221,518 A | 6/1993 | Mills | 422/52 |
| 5,234,824 A | 8/1993 | Mullis | 435/91 |
| 5,237,016 A | 8/1993 | Ghosh et al. | 525/329.4 |
| 5,242,974 A | 9/1993 | Holmes | 525/54.11 |
| 5,262,128 A | 11/1993 | Leighton et al. | 422/100 |
| 5,283,342 A | 2/1994 | Gustavson et al. | 548/304.1 |
| 5,288,644 A | 2/1994 | Beavis et al. | |
| 5,312,233 A | 5/1994 | Tanny et al. | 417/316 |
| 5,338,688 A | 8/1994 | Deeg et al. | 436/180 |
| 5,373,156 A | 12/1994 | Franzen | 250/288 |
| 5,376,788 A | 12/1994 | Standing et al. | 250/287 |
| 5,380,833 A | 1/1995 | Urdea | 536/22.1 |
| 5,381,008 A | 1/1995 | Tanner et al. | 250/288 |
| 5,382,793 A | 1/1995 | Weinberger et al. | 250/288 |
| 5,410,068 A | 4/1995 | Coull et al. | 548/545 |
| 5,430,136 A | 7/1995 | Urdea et al. | 536/243 |
| 5,436,327 A | 7/1995 | Southern et al. | 536/25.34 |
| 5,439,649 A | 8/1995 | Tseung et al. | 422/99 |
| 5,457,041 A | 10/1995 | Ginaven et al. | 435/172.1 |
| 5,474,895 A | 12/1995 | Ishii et al. | 435/6 |
| 5,478,893 A | 12/1995 | Ghosh et al. | 525/329.4 |
| 5,484,701 A | 1/1996 | Cocuzza et al. | 435/6 |
| 5,492,817 A | 2/1996 | Thompson et al. | 435/68.1 |
| 5,498,545 A | 3/1996 | Vestal et al. | |
| 5,503,980 A | 4/1996 | Cantor | 435/6 |
| 5,506,348 A | 4/1996 | Pieles | 536/23.1 |
| 5,510,613 A | 4/1996 | Reilly et al. | 250/287 |
| 5,512,295 A | 4/1996 | Kornberg et al. | 424/450 |
| 5,512,439 A | 4/1996 | Hornes et al. | 435/6 |
| 5,514,548 A | 5/1996 | Krebber et al. | 436/6 |
| 5,527,675 A | 6/1996 | Coull et al. | 435/6 |
| 5,541,313 A | 7/1996 | Ruth | 536/24.3 |
| 5,545,539 A | 8/1996 | Miller | 435/91.2 |
| 5,547,835 A | 8/1996 | Köster et al. | 435/6 |
| 5,580,733 A | 12/1996 | Levis et al. | 435/6 |
| 5,589,136 A | 12/1996 | Northrup et al. | 422/102 |
| 5,599,500 A | 2/1997 | Jones | 422/62 |
| 5,601,982 A | 2/1997 | Sargent et al. | 435/6 |
| 5,604,099 A | 2/1997 | Erlich et al. | 435/6 |
| 5,605,662 A | 2/1997 | Heller | 422/68.1 |
| 5,605,798 A | 2/1997 | Köster et al. | 435/6 |
| 5,612,474 A | 3/1997 | Patel | 536/27.14 |
| 5,622,824 A | 4/1997 | Köster et al. | 435/6 |
| 5,622,829 A | 4/1997 | King et al. | 435/6 |
| 5,624,711 A | 4/1997 | Sundberg et al. | 427/261 |
| 5,625,184 A | 4/1997 | Vestal et al. | |
| 5,627,369 A | 5/1997 | Vestal et al. | |
| 5,631,134 A | 5/1997 | Cantor | 435/6 |
| 5,641,959 A | 6/1997 | Holle et al. | 250/287 |
| 5,643,722 A | 7/1997 | Rothschild et al. | 435/6 |
| 5,643,798 A | 7/1997 | Beavis et al. | 436/94 |
| 5,654,545 A | 8/1997 | Holle et al. | 250/287 |
| 5,663,242 A | 9/1997 | Ghosh et al. | 525/329.4 |
| 5,670,322 A | 9/1997 | Eggers et al. | 435/6 |
| 5,670,381 A | 9/1997 | Jou et al. | 436/518 |
| 5,677,195 A | 10/1997 | Winkler et al. | 436/518 |
| 5,691,141 A | 11/1997 | Köster et al. | 435/6 |
| 5,700,642 A | 12/1997 | Monforte et al. | 435/6 |
| 5,705,813 A | 1/1998 | Apffel et al. | |
| 5,716,825 A | 2/1998 | Hancock et al. | |
| 5,742,049 A | 4/1998 | Holle et al. | 250/282 |
| 5,743,960 A | 4/1998 | Tisone | 118/683 |
| 5,746,373 A | 5/1998 | Sanada | 239/102.2 |
| 5,756,050 A | 5/1998 | Ershow et al. | 422/100 |
| 5,757,392 A | 5/1998 | Zhang | 347/14 |
| 5,760,393 A | 6/1998 | Vestal et al. | 250/282 |
| 5,777,324 A | 7/1998 | Hillenkamp | 250/288 |
| 5,777,325 A | 7/1998 | Weinberger et al. | 250/287 |
| 5,795,714 A | 8/1998 | Cantor et al. | 435/6 |
| 5,807,522 A | 9/1998 | Brown et al. | 422/50 |
| 5,830,655 A | 11/1998 | Monforte et al. | 435/6 |
| 5,864,137 A | 1/1999 | Becker et al. | 250/287 |
| 5,869,240 A | 2/1999 | Patterson | 435/6 |
| 5,869,242 A | 2/1999 | Kamb | 435/6 |
| 5,872,003 A | 2/1999 | Köster | 435/283.1 |
| 5,885,775 A | 3/1999 | Haff et al. | 435/6 |

FOREIGN PATENT DOCUMENTS

| | | |
|---|---|---|
| EP | 0412883 | 2/1991 |
| EP | 0455905 | 11/1991 |
| EP | 0456304 | 11/1991 |
| EP | 0500506 | 8/1992 |
| EP | 0655501 | 5/1995 |
| EP | 0701001 | 3/1996 |
| FR | 2597260 | 10/1987 |
| GB | 2017105 | 3/1979 |
| JP | 63230086 | 9/1988 |
| JP | 2215399 | 8/1990 |
| JP | 6294796 | 10/1994 |
| JP | 8290377 | 11/1996 |
| WO | 8402579 | 7/1984 |
| WO | 8909282 | 10/1989 |
| WO | 8909406 | 10/1989 |
| WO | 8910786 | 11/1989 |
| WO | 8911270 | 11/1989 |

| | | |
|---|---|---|
| WO | 8912694 | 12/1989 |
| WO | 9001564 | 2/1990 |
| WO | 9003382 | 4/1990 |
| WO | 9007582 | 7/1990 |
| WO | 9014148 | 11/1990 |
| WO | 9015883 | 12/1990 |
| WO | 9106678 | 5/1991 |
| WO | 9113075 | 9/1991 |
| WO | 9115600 | 10/1991 |
| WO | 9203575 | 3/1992 |
| WO | 9207879 | 5/1992 |
| WO | 9210092 | 6/1992 |
| WO | 9213629 | 8/1992 |
| WO | 9215712 | 9/1992 |
| WO | 9306925 | 4/1993 |
| WO | 9309668 | 5/1993 |
| WO | 9320236 | 10/1993 |
| WO | 9400562 | 1/1994 |
| WO | 9411529 | 5/1994 |
| WO | 9411530 | 5/1994 |
| WO | 9411735 | 5/1994 |
| WO | 9416101 | 7/1994 |
| WO | 9421822 | 9/1994 |
| WO | 9504524 | 2/1995 |
| WO | 9507361 | 3/1995 |
| WO | 9513538 | 5/1995 |
| WO | 9515001 | 6/1995 |
| WO | 9530773 | 11/1995 |
| WO | 9531429 | 11/1995 |
| WO | 9619587 | 6/1996 |
| WO | 9629431 | 9/1996 |
| WO | 9632504 | 10/1996 |
| WO | 9636731 | 11/1996 |
| WO | 9636732 | 11/1996 |
| WO | 9636986 | 11/1996 |
| WO | 9636987 | 11/1996 |
| WO | 9637630 | 11/1996 |
| WO | 9403499 | 1/1997 |
| WO | 9708306 | 3/1997 |
| WO | 9716699 | 5/1997 |
| WO | 9733000 | 9/1997 |
| WO | 9737041 | 10/1997 |
| WO | 9742348 | 11/1997 |
| WO | 9743617 | 11/1997 |
| WO | 9803684 | 1/1998 |
| WO | 9812355 | 3/1998 |
| WO | 9820019 | 5/1998 |
| WO | 9820020 | 5/1998 |
| WO | 9820166 | 5/1998 |
| WO | 9820200 | 5/1998 |
| WO | 9826095 | 6/1998 |
| WO | 9854751 | 12/1998 |
| WO | 9912040 | 3/1999 |
| WO | 9914375 | 3/1999 |

OTHER PUBLICATIONS

Seela and Kehne, Palinddromic octa– and dodecanucleotides containing 2'–deoxytubercidin: Synthesis, hairpin formation, and recognition by the endodeoxyribonuclease EcoRI, *Biochemistry 26*:2232–2238 (1987).

Bannwarth, Solid–phase synthesis of oligodeoxynucleotides containing phosphoramidate internucleotide linkages and their specific chemcical cleavage, *Helvetica Chimica Acta 71*:1517–1527 (1988).

Matteucci et al., Synthesis of deoxyoligonucleotides on a polymer support, *J. A. Chem. Soc. 103*:3185–3191, 1981.

Mizusawa, et al., "Improvement of the dideoxy chain termination method of DNA sequencing by use of deoxy–7–deazaguanosine triphosphate in place of dGTP", *Nucleic Acid Res.* 14(3):1319–1325 (1986).

Newton et al., "The production of PCR products with 5' single–stranded tails using primers that incorporate novel phospohoramidite intermediates", *Nucl. Acids. Res.* 21:1155–1162 (1993).

Rink, "Solid–phase synthesis of protected peptide fragments using a trialkoxy–diphenyl–methlester resin", *Tetrahedron Lett. 28*:3787–3790 (1987).

Tong et al., Solid–phase method for the purification of DNA sequencing reactions, *Anal. Chem. 64*:2672–2677, (1992).

Wiedmann M. et al., Ligase chain reaction (LCR)—overview and applications, *PCR Methods Appl. 3*(4):S51–S64 (1994).

Beck et al., Chemiluminescent detection of DNA: application for DNA sequencing and hybridization, *Nucl Acids Res 17*:5115–5123 (1989).

Jurinke et al., Application of nested PCR and mass spectrometry for DNA–based virus detection: HBV–DNA detected in the majority of isolated anti–HBc positive sera, *Genetic Analysis 14*:97–102 (1998).

Kozal et al., "Extensive polymorphisms observed in HIV–1 clade B protease gene using high–density oligonucleotide arrays", *Nature Medicine*, 2(7):753–759 (1996).

Kuppuswamy, et al., "Single nucleotide primer extension to detect gentic diseases: experimental application to hemophilia B (factor IX) and cystic fibrosis genes", *Proc. Natl. Acad. Sci. USA* 88:1143–1147 (1991).

Lamture et al., "Direct detection of nucleic acid hybridization on the surface of a charge coupled device", *Nucl. Acids Res.* 22:2121–2125 (1994).

Landegren et al., "DNA Diagnostics—Molecular techniques and automation", *Science 242*:229–237 (1988).

Li et al., "Analysis of single mammalian cell lysates by mass spectrometry", *J. Am. Chem. Soc. 118*:11662–11663 (1996).

Little et al., Detection of RET proto–oncogene codon 634 mutations using mass spectrometry, *J. Mol Med.* 75:745–750 (1997).

Little et al., Identification of apolipoprotein E polymorphisms using temperature cycled primer oligo base extension and mass spectrometry, *Short Communiation*.

Wain–Hobson et al., Nucleotide sequence of the AIDS virus, LAV, *Cell 40*:9–17 (1985).

Walker et al., Multiplex strand displacement amplification (SDA) and detection of DNA sequences from *Mycobacterium tuberculosis* and other mycobacteria, *Nucleic Acids Res.* 22(13):2670–2677 (1994).

Yang, et al., "Detection of hepatitis B virus in plasma using flow cytometric analysis of polymerase chain reaction–amplified DNA incorporating digoxigenin–11–dUTP", *Blood* 81(4):1083–1088 (1993).

Barany F., Genentic disease detection and DNA amplification using cloned thermostable ligase, *Proc. Natl. Acad. Sci.* 88:189–193 (1991).

Ferrie et al., Development, multiplexing, and application of ARMS tests for common mutations in the CFTR gene, *Am. J. Hum. Genet. 51*:251–262 (1992).

Gust et al., Taxomonic classification of Hepatitis A virus *Intervirology 20*:1–7 (1983).

Guyader, et al., "Genome organization and transactivation of the human immunodeficiency virus type 2", *Nature* 326:662–669 (1987).

Lopez–Galindez, et al., "Characterization of genetic variation and 3'–azido–3'–deoxythymidine–resistance mutations of human immunodeficiency virus by the RNase A mismatch cleavage method", *Proc. Natl. Acad. Sci, USA* 88:4280–4284 (1991).

Miyazaki, et al., The first Japanese case of Hb Santa Ana, an unstable abnormal hemoglobin, identified rapidly by electrospray ionization mass spectrometry. *Internal Medicine* 36:365–370 (1997).

Nikiforov et al. "Genetic Bit Analysis: a solid phase method for typing single nucleotide polymorphisms" Nucleic Acids Research, 22(20):4167–4175 (1994).

Saiki, et al., "Genetic analysis of amplified DNA with immobilized sequence–specific oligonucleotide probes", *Proc. Natl. Acad. Sci. USA* 86:6230–6234 (1989).

Zhang et al., "Single–base mutational analysis of cancer and genetic diseases using membrane bound modified oligonucleotides", *Nucl. Acids Res.* 19:3929–3933 (1991).

Arlinghaus et al, "Applications of resonance ionization spectroscopy for semiconductor, environmental and biomedical analysis, and for DNA sequencing", *SPIE*, vol. 1435, *Opt. Methods Ultrasensitive Detect. Anal. Tech. Appl.* pp. 26–35 (1991).

Bains, Setting a sequence to sequence a sequence, *Biotechnology* 10:757–758 (1992).

Broude, Natalia E. et al., "Enhanced DNA sequencing by hybridization (streptavidin/biotin/stacking interaction/T4 DNA ligase/DNA polymerase)", *Proc. Natl. Acad. Sci.*, 91:3072–3076 (1994).

Chait and Kent, Weighing naked proteins: practical, high–accuracy mass measurement of peptides and proteins, *Science* 257:1885–1894 (1992).

Charkrabarti et al., Sequence of Simian Immunodeficiency Virus from Macaque and its Relationship to Other Human and Simian Retroviruses, Nature 328:543–547 (1987).

Chen and Seeburg, Supercoil sequencing: A fast and simple method for sequencing plasmid DNA, *DNA* 4(2):165–170 (1985).

Church et al., "Multiplex DNA Sequencing", *Science* 240:185–188 (1988).

Drmanac, et al., "Sequencing of megabase plus DNA by hybridization: theory of the method", *Genomics* 4:114–128 (1989).

Frank and Köster, DNA chain length and the influence of base composition on electrophoretic mobility of oligodeoxyribonucleotides in polyacrylamide–gels, *Nucl. Acids Res.* 6:2069–2087 (1979).

Fu et al., A DNA sequencing strategy that requires only five bases of known terminal sequence for priming, *Proc. Natl. Acad. Sci. USA* 92:10162–10166 (1995).

Fu et al., Sequencing double–stranded DNA by strand displacement, *Nucl Acid Res* 25:677–679 (1997).

Fu et al., A DNA sequencing strategy which requires only five bases of known terminal sequence for priming, Paper presented, Genome Mapping and Sequencing, Cold Spring Harbor Laboratory.

Higuchi et al., Kinetic PCR analysis: Real–time monitoring of DNA amplification reactions, *Bio/Technology* 11:1026–1030 (1993).

Higuchi et al., A general method of in vitro preparation and mutagenesis of DNA fragments: Study of protein and DNA interactions, *Nucleic Acids Res.* 16:7351–7367 (1988).

Hultman et al., Direct solid phase sequencing of genomic and plasmid DNA using magnetic beads as solid support, *Nucl. Acids Res.* 17:4937–4946 (1989).

Hyman, A new method of sequencing DNA, *Anal. Biochem.* 174:423–436 (1988).

Innis et al., DNA sequencing with *Thermus aquaticus* DNA polymerase and direct sequencing of polymerase chain reaction–amplified DNA, *Proc. Natl. Acad. Sci. USA* 85:9436–9440 (1988).

Jett et al., "High–Speed DNA Sequencing: An Approach Based Upon fluorescence Detection of Single Molecules", *J. Bio Strut &Dynam.* 7(2):301–09 (1989).

Ji et al., Two–dimensional electrophoretic analysis of proteins expressed by normal and cancerous human crypts: Application of mass spectrometry to peptide–mass fingerprinting, *Electrophoresis* 15:391–405 (1994).

Khrapko et al., An oligonculeotide hybridization approach to DNA sequencing, *FEB* 256(1,2):118–122 (1989).

Khrapko et al., "A method for DNA sequencing by hybridiztion with oligonucleotide matrix", *J. DNA Seq. and Mapping* 1:375–388 (1991).

Köster, et al., "Oligonucleotide synthesis and multiplex DNA sequencing using chemiluminescent detection", *Nucleic Acids Research*, Symposium Series No. 24, 318–321 (1991).

Labeit et al., Laboratory methods: A new method of DNA sequencing using deoxynucleoside α–thiotriphophates, *DNA* 5:173–177 (1986).

Lawrance et al., Megabase–scale mapping of the HLA gene complex by pulsed field gel elecrophoresis, *Science* 235:1387–1389 (1987).

Little et al., "Mass spectrometry from miniaturized arrays for full comparative DNA analysis", *Nature Med* 3(12):1413–1416 (1997).

Marshall and Hodgson, "DNA chips: An array of possibilities", *Nature Biotechnology* 16:27–31 (1998).

Martin, "New technologies for large–genome sequencing", *Genome* 31:1073–1080 (1989).

Maxam and Gilbert, Sequencing end–labeled DNA with base–specific chemical cleavages, *Methods in Enzymology* 65:499–560 (1980).

Nakamaye et al., "Direct sequencing of polymerase chain reaction amplified DNA fragments through the incorporation of deoxymucleoside α–thiotriphosphates", *Nucleic Acids Res.* 16(21):9947–9959 (1988).

O'Donnell et al., "MassArray as an Enabling Technology for the Industrial–Scale Analysis of DNA" *Genetic Engineering News* 17(21) (1997).

O'Donnell–Maloney et al., The development of microfabricated arrays for DNA sequencing and analysis, *TIBTECH* 14:401–407 (1996).

O'Donnell–Maloney et al., Microfabrication and array technologies for DNA sequencing and diagnostics, *Genetic Analysis: Biomolecular Engineering* 13: 151–157 (1996).

Ornstein et al., Sequencing DNA using $^{35}$S–labeling: A troubleshooting guide, *Biotechniques* 3:476–483 (1985).

Prome et al., Use of combined mass spectrometry methods for the characterization of a new variant of human hemoglobin: The double mutant hemoglobin villeparisis beta 77(EF1), *J. American Society for Mass Spect* 7(2):163–167 (1996).

Raftery, et al., Characterization of a mutant recombinant S100 protein using electrospray ionization mass spectrometry. *Rapid Comm. Mass Spec.* 11:405–409 (1997).

Ratner et al., Complete nucleotide sequence of the AIDS virus, HTLV–III, *Nature* 313:227–284 (1985).

Sanger et al., DNA sequencing with chain–terminating inhibitors, *Proc. Natl. Acad. Sci.* 74:5463–67 (1977).

Smith et al., Fluorescence detection in automated DNA sequence analysis, *Nature* 321:674–679 (1986).

Stahl, et al., "Solid phase DNA sequencing using the biotin–avidin system", *Nucleic Acids Res.* 16(7):3025–3039 (1988).

Strezoska, et al., "DNA sequencing by hybridization: 100 bases read by a non–gel–based method", *Proc. Natl. Acad. Sci. USA* 88:10089–10093 (1991).

Swerdlow and Gesteland, Capillary gel electrophoresis for rapid, high resolution DNA sequencing, *Nucleic Acids Res.* 18(6):1415–1419 (1990).

Tabor and Richardson, DNA sequence analysis with a modified bacteriophage T7 DNA polymerase, *Proc. Natl. Acad. Sci.* 84:4767–4771 (1987).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal chem* 69:4540–4546 (1997).

Moini et al., "A Moving Belt Device to Couple High–Performance Liquid Chromatography and Chemical Reaction Interface Mass Spectrometry", *Bio Mass Spect* 20:308–312 (1991).

Ruppert et al., "Preparation of plasmid DNA as Sequencing Templates in a Microtiter Plate Format", Paper presented, Cold Spring Harbor Laboratory, N.Y. May 10–14, 1995.

Ruppert et al., "A rapid and high throughput method for plasid isolations", Presented: Automation in Mapping and DNA Sequencing Conference, Aug. 31—Sep. 2, 1994.

Ruppert et al., A filtration method for plasmid isolation using microtiter filter plates, *Anal. Biochem.* 230:130–134 (1995).

Trainor, "DNA Sequencing, Automation, and the Human Genome", *Anal. Chem.* 62:418–426 (1990).

Zimmermann et al., Automated preparation and purification of M13 templates for DNA sequencing, *Meth. Mol. Cell. Biol.* 1:29–34 (1989).

Wallace, "Ink–jet based fluid microdispensing in biochemical applications", Microfab Technologies, Inc., Laboratory Automation News, 1(5):6–9 (1996).

Alimpiev et al., Laser desorption mass spectrometry from frozen water solutions using a 3.28 μm YAG/OPO laser system, Proceedings from the 44th ASMS Conference on Mass Spectrometry, p. 644.

Berkenkamp et al., Infrared MALDI–MS of large nucleic acids, Proceedings of the 46th ASMS Conference on Mass Spectrometry and Allied Topics, Orlando, Florida, May 31–Jun. 4, 1998.

Berkenkamp et al., Water as a matrix in infrared MALDI–MS, Proceedings of the 43rd ASMS Conference on Mass Spectrometry and Allied Topics, p. 1247, Atlanta, Georgia, May 1995.

Berkenkamp et al., Performance of infrared matrix–assisted laser desorption/ionization mass spectrometry with lasers emitting in the 3 μm wavelength range, *Rapid Commun. Mass Spectrom.* 11:1399–1406 (1997).

Berkenkamp et al., Infrared MALDI mass spectrometry of large nucleic acids, *Science* 281:260–2 (1998).

Berkenkemp et al., Ice as a matrix for IR–matrix–assisted laser desorption/ionization: mass spectra from a protein single crystal, *Proc. Natl. Acad. Sci. USA* 93:7003–7007 (1996).

Caldwell et al., Mid–infrared matrix assisted laser desorption ionization with a water/glycerol matrix, *Applied Surface Science* 127–129:242–247 (1998).

Eckerskorn et al., High–sensitivity peptide mapping by micro–LC with on–line membrane blotting and subsequent detection by scanning–IR–MALDI mass spectrometry, *J of protein Chem* 16(5):349–362 (1997).

Ehring et al., Photochemical versus thermal mechanisms in matrix–assisted laser desorption/ionization probed by back side desorption, *Rapid Comm in Mass Spect* 10:821–824 (1996).

Kambara, Characteristics of molecular secondary ion mass spectrometry, *Springer Ser. Chem. Phys.* 36:357–362 (1984).

Li et al., Pulsed laser desorption method for volatilizing thermally labile molecules for supersonic jet spectroscopy, *Rev. Sci. Instrum.* 59:557–561 (1988).

Nelson et al., "Volatilization of High Molecular Weight DNA by Pulsed Laser Ablation of Frozen Aqueous Solutions", *Science* 246:1585–1587 (1989).

Pierce ImmunoTechnology Catalog, p. 57 (1993).

Pierce Catalog, pp. T123–T154, 1994.

Smith et al., Capillary zone electrophoresis–mass spectrometry using an electrospray ionization interface, *Anal. Chem.* 60:436–441 (1988).

Takayama, *Org. Mass Spectrom.* 26:1123–1124 (1991).

Wolter et al., Influence of the matrix on the analysis of small oligoribonucleotides by fast atom bombardment mass spectrometry, *J. Mass Spectorm.* 30:485–491 (1995).

Yamashita et al., Electrospray ion source. Another variation on the free–jet theme, *J. Phys. Chem.* 88:4451–4459, (1984).

Yoshida et al., Detection of high mass molecular ions by laser desorption time–of–flight mass spectrometry, *Shitsuryo bunseki* 36:59–69 (1988).

Zhang et al., Exploring infrared wavelength matrix–assisted laser desorption/ionization of proteins with delayed–extraction time–of–flight mass spectrometry, *J. Am. Soc. Mass Spectrom.* 9:879–884 (1998).

Agrawal et al., Efficient methods for attaching non–radioactive labels to the 5' ends of synthetic oligodeoxyribonucleotides, *Nucleic Acids Res.* 14:6227–6245 (1986).

Beaucage et al., The synthesis of modified oligonucleotides by the phosphoramidite approach and their applications, *Tetrahedron* 49:6132–6194 (1993).

Beck et al., Applications of dioxetane chemiluminescent probes to molecular biology, *Anal. Chem.* 62:2258–2270 (1990).

Connolly, B. A., "Oligonucleotides containing modified bases", *Oligonucleotides and Analogues, A Practical Approach*, Edited by F. Eckstein, Oxford University Press, Ch. 7, pp. 40–45 (1991).

Eckstein and Goody, Synthesis and properties of diastereoisomers of adenosine 5'–(O–1–thiotriphosphate) and adenosine 5'–(O–2–thiotriphosphate), *Biochemistry* 15(8):1685–1691 (1976).

Eckstein, Nucleoside phosphorothioates, *Ann. Rev. Biochem.* 54:367–402 (1985).

Eckstein (ed.), *Oligonucleotides and Analogues*, IRL Press, Oxford (1991).

Eckstein, F., Phosphorothioate analogues of nucleotides, *Accounts Chem. Res.* 12:204–210 (1979).

Eggers et al., "A microchip for quantitative detection of molecules utilizing luminescent and radioisotope reporter groups", *Bio Techniques* 17:516–524 (1994).

Hobbs and Eckstein, A general method for the synthesis of 2'–azido–2'deoxy–and 2' amino–2'–deoxyribofuranoxyl purines, *J. Org. Chem.* 42:714–719 (1976).

Hsiung et al., A new simpler photoaffinity analogue of peptidyl rRNA, *Nucl Acids Res* 1:1753–1762 (1974).

Köster et al., N–acyl protecting groups for deoxynucleotides: A quantitative and comparative study, *Tetrahedron* 37:363–369 (1981).

Manoharan et al., A 2'–O–thiol tether in the ribose moiety of nucleic acids for conjugation chemistry, *Gene*, 149:147–156 (1994).

Olejnik et al., "Photocleavable biotin phosphoramidite for 5'–end–labeling, affinity purification and phosphorylation of synthetic oligonucleotides", *Nucleic Acids Res.* 24:351–366 (1996).

*Oligonucleotides and Analogues: A Practical Approach*, Eckstein, ed., Oxford University Press Ch. 3, pp. 49–59, 137–139, 255–259 (1991).

Sasaki et al., Introduction of an azide group into some uridine derivatives via 2',3'–benzoxonium and 2',3'–azidonium intermediates, *J. Org. Chem.* 41:3138–3143 (1976).

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res.* 23(9):1570–1575 (1995).

Singh et al., Oligonucleotides, part 5 + : synthesis and fluorescence studies of DNA oligomers d(AT)$_5$ containing adenines covalently linked at C–8 with dansyl fluorophore, *Nucleic Acids Res.* 18(11):3339–3345 (1990).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Slim et al., Configurationally defined phosphorothioate–containing oligoribonucleotides in the study of the mechanism of cleavage of hammerhead ribozymes, *Nucleic Acids Res.* 19:1183–1188 (1991).

Sproat et al., The synthesis of protected 5'–amino–2', 5'–dideoxyribonucleoside–3'–O–phosphoramidites; applications of 5'–amino–oligodeoxyribonucleotides, *Nucleic Acids Res.* 15:6181–6196 (1987).

Sproat et al., The synthesis of protected 5'–mercapto–2', 5'–dideoxyribonucleoside–3'–O–phosphoramidites; uses of 5'mercapto–oligodeoxyribonucleotides, *Nucleic Acid Res.* 15:4837–4848 (1987).

Wellhöner et al., Uptake and concentration of bioactive macromolecules by K562 cells via the transferrin cycle utilizing an acid–labile transferrin conjugate, *J. Biol. Chem.* 256:4309–4314, (1991).

Zuckermann et al., Efficient methods for attachment of thiol specific probes to the 3'–ends of synthetic oligodeoxyribonucleotides, *Nucleic Acids Research*, 15:13, 5305–5321 (1987).

Alderton et al., Magnetic bead purification of M13 DNA sequencing templates, *Anal. Biochem.* 201:166–169 (1992).

Arshady, Reza; Review: Beaded Polymer Supports and Gels, I. Manufacturing Techniques; Journal of Chromatography, 586 (1991); pp. 181–197.

Arshady, Reza, Beaded polymer supports and gels: II. Physico–chemical criteria and functionalization, *Journal of Chromatography*, 586:199–219 (1991).

Batista–Viera et al., A new method for reversible immobilization of thiol biomolecules bsed on solid–phase bound thiosulfonate groups, *App. Biochem and Biotech*, 31:175–195 (1991).

Brown, et al., "A single–bead decode strategy using electrospray ionization mass spectrometry and a new photolabile linker: 3–amino–3–(2–nitrophenyl) propionic acid", *Mol. Diversity* 1:4–12(1995).

Chrisey et al., Fabrication of patterned DNA surfaces, *Nucl. Acids. Res.* 24:3040–3047 (1996).

Chrisey et al., Covalent attachment of synthetic DNA to self–assembled monlayer films, *Nucl. Acids Res.* 24:3031–3039 (1996).

Damha, Masad J. et al., An improved procedure for derivatization of controlled–pore glass beads for solid–phase oligonucleotide synthesis; *Nucleic Acids Research* 18(13):3813–3821 (1990).

Fujita et al., Surprising lability of biotin–streptavidin bond during transcription of biotinylated DNA bound to paramagnetic beads, *BioTechniques* 14:608–617 (1993).

Ghosh, et al., "Covalent attachment of oligonucleotides to solid supports", *Nuc. Acids. Res.* 15)13):5353–5372 (1987).

Gildea et al., A versatile acid–labile linker for modification on synthetic biomolecules, *Tetrahedron Letters* 31:7095–7098 (1990).

Goldmacher et al., Photoactivation of toxin conjugates, *Bioconjugate Chem.* 3:104–107, (1992).

Hayashi, et al., "Immobilization Thiol Proteases onto porous poly(vinyl alcohol) beads", *Polymer Journal*, 25(5):489–497 (1993).

Hazum et al., A photocleavable protecting group for the thiol function of cysteine, *Pept., Proc. Eur. Pept. Symp., 16th*, Brunfeldt, K (Ed), pp. 105–110 (1981).

Heermann, et al., "Liquid–phase hyridization and capture of hepatitis B virus DNA with magnetic beads and fluorescence detection of PCR product", *J. of Virol. Methods* 50:43–58 (1994).

Hornes and Korsnes, Magnetic DNA hybridization of oligonucleotide probes attached to superparamagnetic beads and their use in the isolation of Poly(A) mRNA from eukaryotic cells, *GATA* 7:145–150, (1990).

Köster et al., Polymer support oligonucleotide synthesis—XV[1,2], *Tetrahedron* 40:102–112 (1984).

Lund, Vera et al., "Assessment of methods for covalent binding of nucleic acids to magnetic beads, dynabeads, and the characteristics of the bound nucleic acids in hybridization reactions", *Nucleic Acids Res.* 16(22) (1988).

McCray and Trentham, "Properties and uses of photoreactive caged compounds", *Annu. Rev. Biophys. Biophys. Chem.* 18:239–270 (1989).

Nikiforov and Rogers, "The use of 96–well polystyrene plates for DNA hybridization–based assays: An evaluatin of different approaches to oligonucleotide immobilization", *Anal. Biochm.* 227:201–209 (1995).

O'Donnell et al., High–density, covalent attachment of DNA to siliocn wafers for analysis by MALDI–TOF mass spectrometry, *Analytical Chemistry* 69:2438–2443 (1997).

Pon, Richard T. et al.; Research Report: Derivatization of Controlled Pore Glass Beads for Solid Phase Oligonucleotide Systhesis; BioTechniques vol. 6, No. 8 (1988); pp. 768–770, 773–775.

Rasmussen et al., "Covalent immobilization of DNA onto polystyrene microwells: The molecules ar eonly bound at the 5' end", *Anal. Biochem.* 198:138–142 (1991).

Running and Urdea, "A procedure for productive coupling of synthetic oligonucleotides to polystyrene microtiter wells for hybridization capture", *Biotechniques* 8:276–277 (1990).

Senter et al., Novel photocleavable protein crosslinking reagents and their use in the preparation of antibody–toxin conjugates, Photochem. Photobiol. 42:231–237, (1985).

Sinha et al., Polymer support oligonucleotide synthesis XVII: Use of B–cyanoethyl–N, N–dialkylamino–/N–morpholino phosphoramidite of deoxynucleosides for the synthesis of DNA fragments simplifying deprotection and isolation of final product, *Nucleic Acids Res.* 12:4539 (1984).

Thuong and Asseline, Oligonucleotides attached to intercalators, photoreactive and cleavage agents, *Oligonucleotides and Analogues: A Practical Approach*, Eckstein, edr., Oxford University Press Ch. 12, pp. 283–308 (1991).

Wang, Solid phase synthesis of protected peptides via photolytic cleavage of the α–methylphenacyl ester anchoring linkage, *J. Org. Chem.* 41(20):3258–3261 (1976).

Wong, Ch. 12: Conjugation of proteins to solid matrices, *Chemistry of Protein Conjugation and Cross Linking* 12:295–317 (1993).

Yen et al., Synthesis of water–soluble copolymers containing photocleavable bonds, *Makromol. Chem.* 190:69–82 (1989).

Bornsen et al., Influence of solvents and detergents on matrixj–assisted laser desorption/ioniation mass spectrometry measurements of proteins and oligonucleotides, *Rapid Comm. Mass. Spectrom.* 11:603–609 (1997).

Chan et al., Matrix–assisted laser desorption/ionization using a liquid matrix: formation of high–mass cluster ions from proteins, *Org. Mass Spectrom.* 27:53–56 (1992).

Cornett et al., Liquid mixtures for matrix–assisted laser desorptioin, 65:2608–2613 (1993).

Cramer et al., Analysis of phospho– and glycopolypeptides with infrared matrix–assisted laser desorption and ionization, *Anal. Chem.* 70:4939–4944 (1998).

Fu et al., Sequencing exons 5 to 8 of the p53 gene by MALDI–TOF mass spectrometry, *Nat Biotechnol* 16:381–4 (1998).

Fu et al., Efficient preparation of short DNA sequence ladders potentially suitable for MALDI–TOF DNA sequencing, *Genetic Analysis* 12:137–142 (1996).

Gruić–Sovulj I. et al., Matrix–assisted laser desorption/ionisation mass spectrometry of transfer ribonucleic acids isolated from yeast, *Nucleic Acids Res.* 25(9):1859–61 (1997).

Haglund et al., Marix–assisted laser–desorption mass spectrometry of DNA using an infrared free–electron laser, *SPIE* 1854:117–128 (1993).

Hillenkamp, MALDI–MS with other wavelengths: options, potentials and limitations, Proceedings of the 46th ASMS Conference on Mass Spectrometry and Allied Topics, Oraldno, Florida, p. 796, May 31–Jun. 4, 1998.

Hillenkamp et al., Matrix Assisted UV–Laser Desorption/Ionization: A New Approach to Mass Spectrometry of Large Biomolecules, *Biological Mass Spectrometry*, Editors: A. L. Burlingame and J. A. McCloskey, Elsevier Science Publishers, B. V., Amsterdam, pp. 49–61 (1989).

Hillenkamp and Karas, Matrix–assisted laser desorption/ionization mass spectrometry of biopolymers, *Anal. Chem* 63(24):1193–1203 (1991).

Hillenkamp, et al., Matrix assisted UV–laser desorption/ionization: A new approtach to mass spectrometry of large biomolecules, In *Biological Mass Spectrometry* (Burlingame and McCloskey, eds.), Elsevier, Amsterdam (1989).

Hunter et al., Frozen–solution MALDI mass spectrometry studies of DNA,. *Proc. SPIE–Int. Soc. Opt. Eng.* 2680:384–389 (1996).

Huth–Fehre et al., Matrix–assisted laser desorption mass spectrometry of oligodeoxythymidylic acids, *Rapid Comm in Mass Spect* 6:209–213 (1992).

Jespersen et al., *Mass Spectrom. in Biol Sci*, Burlingame, ed. p. 217 (1996).

Juhasz et al., Applications of delayed extraction matrix–assisted laser desorption ionization time–of–flight mass spectrometry to oligonucleotide analysis, *Analy Chem* 68:941–946 (1996).

Jurinke et al., Analysis of ligase chain reaction products via matrix–assisted laser desorption/ionization time–of–flight–mass spectrometry, *Analy Biochem* 237:174–181 (1996).

Jurinke et al., Recovery of nucleic acids from immobilized biotin–streptavidin complexes using ammonium hydroxide and applications in MALDI–TOF mass spectrometry, *Anal. Chem.* 69:904–910 (1997).

Jurinke et al., Detection of hepatitis B virus DNA in serum samples via nested PCR and MALDI–TOF mass spectrometry, *Genetic Analysis* 13:67–71 (1996).

Kim et al., Investigation of porphyrins and metalloporphyrins by liquid matrix–assisted laser desorption mass spectrometry, *Mikrochim. Acta* 113:101–111 (1994).

Kirkepar et al., Matrix Assisted Laser Desorption/Ionization Mass Spectrometry of Enzymatically Synthesized RNA up to 150 kDa, Nucl. Acids Res. 22:3866–3870 (1994).

Kirpekar et al., "7–deaza purine bases offer a higher ion stability in the analysis of DNA by matrix–assisted laser desorption/ionization mass spectrometry" *Rapid Commun. Mass Spectrom.* 9:525–531 (1995).

Kirpekar et al., DNA sequence analysis by MALDI mass spectrometry, *Nucleic Acids Res.* 26:2554–9 (1998).

Kussman et al., Matrix–assisted Laser Desorption /Ionization Mass Spectrometry Sample Preparation Techniques Designed for Various Peptide and Protein Analytes, J. Mass Spectrom. 32:593–601 (1997).

Li et al., "High–Resolution MALDI Fourier Transform Mass Spectrometry of Oligonucleotides", *Anal Chem* 68(13):2090–2096 (1996).

Little et al., Direct detection of synthetic and biologically generated double–stranded DNA by MALDI–TOF MS, *J. Mass Spec* 17:1–8 (1997).

Liu et al., Use of nitrocellulose film substrate in matrix–assisted laser desorption/ioniation mass spectrometry for DNA mapping and screening, *Anal. Chem.* 67:3482–3490 (1995).

Nordhoff et al., Direct mass spectrometric sequencing of low–picomole amounts of oligodeoxynucleotides iwth up to 21 bases by matrix–assisted laser desorption/ionization mass spectrometry, *J. Mass Spectrom.* 30:99–112 (1995).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial 181–197* (1992).

Pieles et al., Matrix–assisted laser desorption ionization time–of–flight mass spectrometry: a powerful tool for the mass and sequence analysis of natural and modified oligonucleotides, *Nucleic Acids Res.* 21:3191–3196 (1993).

Ross et al., Analysis of short tandem repeat polymorphisms in human DNA by matrix assisted laser desorption/ionization mass spectrometry, *Anal. Chem.* 69:3966–3972 (1997).

Shaler et al., "Effect of Impurities on the matrix–Assisted Laser Desorption Mass Spectra of Single–Stranded Oligodeoxynucleotides", *Anal. Chem.* 68:576–579 (1996).

Shaler et al., "Analysis of enzymatic DNA sequencing reactions by matrix–assisted laser desorption/ionization time–of–flight mass spectrometry", *Rapid Commun Mass Spectrom* 9(10):942–947 (1995).

Siegert et al., Matrix–assisted laser desorption/ionization time–of–flight mass spectrometry for the detection of polymerase hain reaction products containing 7–deasapurine moieties, *Anal. Biochem.* 243:55–65 (1996).

Tang et al., Detection of 500–nucleotide DNA by laser desorption mass spectrometry, *Rapid Commun. Mass Spectrom.* 8:727–730 (1994).

Tang et al., Matrix–assisted laser desorption/ionization of restriction enzyme–digested DNA, *Rapid Commun. Mass Spectrom.* 8:183–186 (1994).

Tang et al., "Matrix–assisted laser desorption/ionization mass spectrometry of immobilized duplex DNA probes", *Nucleic Acids Research* 23:3126–3131 (1995).

Tang, et al., Improving mass resolution in MALDI/TOF analysis of DNA.

Tsarbopoulous et al., Comparative mapping of recombinant proteins and glycoproteins by plasma desorption and matrix–assisted laser desorption/ionization mass spectrometry, *Anal. Chem.* 66:2062–2070 (1994).

Vorm et al., Improved resolution and very high sensitivity in MALDI TOF of matrix surfaces made by fast evaportion, *Anal. Chem.* 66:3281–3287 (1994).

Williams et al., p–Nitroaniline/glycerol: a binary liquid matrix for matrix–assisted laser desorption/ionization analysis, *Eur. Mass. Spectrom.* 4:379–383.

Wu et al., Matrix–assisted Laser Desorption Time–of–flight Mass Spectrometry of Oligonucleotides Using 3–Hydroxypicolinic Acid as an Ultraviolet–sensitive Matrix, *Rapid Comm Mass Sepc* 7:142–146 (1993).

Wu et al., Time–of–Flight Mass Spectrometry of Underivatized Single–Stranded DNA Oligomers by Matrix–Assisted Laser Desorption, *Anal. Chem.* 66:1637–1645 (1994).

Yau et al., Threshold fluences for productin of positive and negative ions in matirx–assisted laser desorption/ionisation using liquid and solid matrices, *Chem. Phys. Lett.* 202:93–100 (1993).

Berkenkamp et al, *Proc. Natl. Acad. Sci. USA* 93:7003 (1996).

Berkenkamp et al., *Rapid Comm. Mass Spectrom.* 11:1399–1406 (1997).

Hillenkamp et al., MALDI–MS in the infrared: a critical evaluation, Proceedings of the 43rd ASMS Conference on Mass Spectrometry and Allied Topics, p. 357, Atlanta, Georgia, May 1995.

Kirpekar et al., Double stranded DNA analysed by UV–and IR–MALDI–MS, Proceedings of the 46th ASMS Conference on Mass Spectrometry and Allied Topics, p. 1004, Orlando, Forida, May 31–Jun. 4, 1998.

Menzel et al., New developments in IR–MALDE–MS with a TEA–$CO_2$–Laser, Proceedings of the 46th ASMS Conference on Mass Spectrometry and Allied Topics, p. 797, Orlando, Florida, May 31–Jun. 4, 1998.

Menzel et al., IR–MALDI–MS in the $3\mu$m wavelength region with lasers of different pulse width, Proceedings of the 46th ASMS Conference on Mass Spectrometry and Allied Topics, Orlando, Florida, p. 922, May 31–Jun. 4, 1998.

Niu et al., Direct comparison of infrared and ultraviolet wavelength matrix–assisted laser desorption/ionization mass spectrometry of proteins, *J Am Soc Mass Spectrom* 9:1–7 (1998).

Nordhoff et al., Ion stability of nucleic acids in infrared matrix–assisted laser desorption/ionization mass spectrometry, *Nuc Acids Res.* 21:3347–3357 (1993).

Nordhoff et al., Comparison of IR– and UV–matrix–assisted laser desorption/ionization mass spectrometry of oligodeoxynucleotides, *Nuc Acids Res* 22(13):2460–2465 (1994).

Nordhoff et al., Matrix–assisted laser desorption/ionization mass spectrometry of nucleic acids with wavelengths in the ultraviolet and infrared, *Rapid Comm in Mass Spectorm.* 6:771–776 (1992).

Overberg et al., Matrix–assisted laser desorption of large biomolecules with a TEA–$CO_2$–laser, *Rapid Comm in Mass Spectro* 5(3):128–131 (1991).

Overberg et al., Matrix–assisted infrared–laser (2.94 um) desorption/ionization mass spectrometry of large biomolecules, *Rapid Comm in Mass Spectrom.* 4:293 (1990).

Sadeghi, *Rapid Comm. Mass Spectrom.* 11:393 (1997).

Siegel et al., Determination of distribution and loading values for calicheamicin derivatives conjugated to antibodies by matrix–assisted infrared–laser desorption/ionization mass spectrometry, Proceedings of the 42nd ASMS Conference on Mass Spectrometry, p. 967, May 19–Jun. 3, 1994.

Siegel et al., Calicheamicin derivatives conjugated to monoclonal antibodies: determination of loading values and distributions by infrared and UV matrix–assisted laser desorptioin/ionization mass spectrometry and electrospray ionization mass spectrometry, *Anal. Chem.* 69:2716–2726 (1997).

Strupat et al., Infrared–matrix–assisted laser desorption/ionization mass spectrometry (IR–MALDI–MS) of proteins electroblotted onto polymer membranes after SDS–PAGE separation, *Mass Spectrometry in the Biological Sciences* Burlingame and Carr, eds. Humana Press, pp. 203–216 (1995).

Strupat et al., Matrix–assisted laser desorption ionization mass spectrometry of proteins electroblotted after polyacrylamide gel electrophoresis, *Anal. Chem.* 66:464–470 (1994).

Sutton et al., The analysis of myocardial proteins by infrared and ulravilet laser desorption mass spectrometry, *Electrophoresis* 18:424–431 (1997).

Aberth et al., Secondary ion mass spectrometry with cesium ion primary beam and liquid target matrix for analysis of bioorganic compounds, *Anal. Chem.* 54:2029–2034 (1982).

Andersen, et al., Electrospray ionization and matrix assisted laser desorption/ionization mass spectrometry: Powerful analytical tools in recombinant protein chemistry, *Nature Biotech.* 14:449–457 (1996).

Ardey, Electrospray mass spectrometry, *Spectroscopy Europe,* 4:10–20 (1992).

Bai et al., Procedures for detection of DNA by matrix–assisted laser desorptioin/ionization mass spectrometry using a modified nation film substrate, *Rapid Comm. Mass Spectrom* 9:1172–1176 (1995).

Bains, DNA sequencing by mass spectrometry: Outline of a potential future application, *Chimicaoggi* 9:13–16 (1991).

Barrell B., "DNA sequencing: present limitations and prospects for the future", *FASEB Journal* 5:40–45 (1991).

Braun et al., Detecting CFTR gene mutations by using primer oligo base extension and mass spectrometry, *Clinical Chemistry* 43:1151–1158 (1997).

Braun et al., "Improved Analysis of Microsatellites Using Mass Spectrometry", *Genomics* 46:18–23 (1997).

Brennan et al., New methods ot sequence DNA by mass spectrometry, *SPIE*, vol. 1206, *New Technol. Cytom. Mol. Biol.* pp. 60–77 (1990).

Chen et al., Trapping, detection, and mass determination of coliphage T4 DNA ions of $10^8$ Da by electrospray ionization fourier transorm ion cyclotron resonance mass spectrometry, *Anal. Chem.* 67:1159–1163 (1995).

Covey, et al., The determination of protein, oligonucleotide and peptide molecular weights by ion–spray mass spectrometry, *Rapid Comm. Mass Spectrom.* 2:249–256 (1988).

Crain, Mass spectrometric techniques in nucleic acid research, *Mass Spectrom. Rev.* 9:505–554 (1990).

Dass et al., Particle beam induced reactions between peptides and liquid matrices, *Anal. Chem.* 60:2723–2729 (1988).

Edmonds et al., Thermospray liquid chromatography–mass spectrometry of nucleosides and of enzymatic hydrolysates of nucleic acids, *Nucleic Acids Research* 13:8197–8206 (1985).

Fenn, et al., Electrospray ionization for mass spectrometry of large biomolecules, *Science* 246:64–71 (1989).

Fuerstenau & Brenner, Molecular weight determination of megadalton DNA electrospray ions using charge detection time–of–flight mass spectrometry, *Rapid Comm. Mass Spectrom.* 9:1159–1163 (1995).

Ganem et al., Detection of oligonucleotide duplex forms by ion–spray mass spectrometry, *Tetrahedron Letters* 34:1445–1448, (1993).

Gross et al., Investigations of the metastable decay of DNA under ultraviolet matrix–assisted laser desorption/ionization conditions with post–source–decay analysis and hydrogen/deuterium exchange, *J Amer Soc for Mass Spect* 9:866–878 (1998).

Grotjahn et al., Sequencing of oligodeoxyribonucleotides by negative FAB–MS, *Int. J. Mass. Spectrom. Ion Phys.* 46:439–442 (1983).

Grotjahn, Oligonucleotide sputtering from liquid matrices, Springer Proc. Phys. 9:118–125 (1986).

Harada et al., Diethanolamine assisted secondary ion mass spectrometry of naturally occurring complex oligosaccharides, *Org. Mass Spectrom.* 17:386–391 (1982).

Hillenkamp and Ehring, Laser desorption mass spectrometry Part 1: Basic mechanisms and techniques, *Mass Spectrometry in the Biological Sciences: A tutorial*, pp. 165–179 (1992).

Jacobson, et al. Applications of mass spectrometry to DNA sequencing, *GATA* 8:223–229 (1991).

Karas & Hillenkamp, Laser desorption ionization of proteins with molecular masses exceeding 10 000 daltons, *Anal. Chem.* 60:2299–3001 (1988).

Köster et al., "A strategy for rapid and efficient DNA sequencing by mass spectrometry", *Nature Bio* 14:1123–1128 (1996).

Kovacik et al., Liquid secondary ion mass spectrometry of methyl glycosides of oligosaccharides using matrices containing carboxamides, *Rapid Comm. Mass. Spectrom.* 10:1661–1667 (1996).

Laramee et al., Evidence for radical anion formation during liquid secondary ion mass spectrometry analysis of oligonucleotides and synthetic oligomeric analogues: a deconvolution algorithm for molecular ion region clusters, *Anal. Chem.* 61:2154–2160 (1989).

Limbach et al., Molecular mass measurement of intact ribonucleic acids via electrospray ionization quadrupole mass spectrometry, *J. Am. Soc. Mass Spectrom* 6:27–39 (1995).

Little et al., Verification of 50– to 100–mer DNA and RNA sequences with high–resolution mass spectrometry, *Proc. Natl. Acad. Sci. USA* 92:2318–2322 (1995).

Monforte and Becker, High–througput DNA analysis by time–of–flight mass spectrometry, *Nature Medicine* 3:360–362 (1997).

Mosca et al., Mass spectrometry and DNA analysis, *Hemoglobin* 17(3):261–268 (1993).

Muddiman et al., Characterization of PCR products from Bacilli using electrospray ionization FTICR mass spectrometry, *Anal. Chem.* 68:3705–3715 (1996).

Murray, "DNA sequencing by mass spectrometry", *J. Mass. Spect.* 31:1203–1215 (1996).

Nelson et al., Time–of–flight mass spectrometry of nucleic acids by laser ablation and ionization from a frozen aqueous matrix, *Rapid Communications in Mass Spectrometry* 4:348–351 (1990).

Nordhoff, et al., Mass spectrometry of nucleic acids, *Mass Spectrom. Rev.* 15:67–138 (1977).

Pomerantz et al., Determination of oligonucleotide composition from mass spectrometrically measured molecular weight, *Am. Soc. Mass Spectrom.* 4:204–09 (1993).

Schram, Karl H., "Mass Spectrometry of Nucleic Acid Components", *Bio Appl of Mass Spect.* 34:203–287 (1990).

Siuzdak, The emergence of mass spectrometry in biochemical research, *Proc. Natl. Acad. Sci. USA* 91:11290–11297 (1994).

Smith R. D., New Developments in Biochemical Mass Spectrometry: Electrospray Ionization, *Anal. Chem.* 62:882–889 (1990).

Spengler et al., *J. Phys. Chem.* 96:9678 (1992).

Stults and Marsters, *Rapid Comm. Mass Spectrom.* 5:359–363 (1991).

Sunner et al., Graphite surface–assisted laser desorption/ionization time–of–flight mass spectrometry of peptides and proteins from liquid solutions, *Anal. Chem.* 67:4335–4342 (1995).

Tomer et al., "Coaxial Continuous Flow Fast Atom Bombardment for Higher–Molecular–Weight Peptides: Comparison with Static Fast Atom Bombardment and electrospray Ionization", *Bio Mass Spect* 20:783–788 (1991).

Valaskovic, et al., Attomole–sensitivity electrospray source for large–molecule mass spectrometry, *Anal. Chem.* 67:3802–3805 (1995).

Valaskovic et al., "Attomole protein characterization by capillary electrophoresis–mass spectrometry", *Science* 273:1199–1202 (1996).

Williams, Time of flight mass spectrometry of DNA laser–ablated from frozen aqueous solutions: applications to the Human Genome Project, *Intl. J. Mass Spectrom. and Ion Processes* 131:335–344 (1994).

Wolter et al., Negative ion FAB mass spectrometric analysis of non–charged key intermediated in oligonucleotide synthesis: rapid identification of partially protected dinucleoside monophosphates, *Biomedical Environmental Mass Spectrometry* 14:111–116 (1987).

Yates, III, Mass spectrometry and the age of the proteome, *J. Mass Spec.* 33:1–19 (1998).

Dale et al., Graphite/liquid mixed matrices for laser desorption/ionization mass spectrometry, *Anal. Chem.* 68:3321–3329 (1996).

Fabris et al., Massive cluster impact ionization on a four sector tandem mass spectrometer, *J. Mass Spect.* 30:140–143 (1995).

Jiang et al., The liquid matrix effects for determination of oligosaccharides by LSIMS, *Chin. Sci. Bull.* 37:1431–1435.

Kolli et al., A new matrix for matrix–assisted laser desorption/ionization in magnetic sector instruments with point detectors, *Rapid Commun. Mass Spectrom* 10:923–926 (1996).

Sequenom Reports On Use of Its DNA MassArray™ Technology to Analyze Genes Associated with Alzheimer's Disease and Arteriosclerosis, Press Release: Sep. 22, 1997, http://www.sequenom.com/pressrelease.htm.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Sequenom Advances the Industrial Genomics Revolution with the Launch of Its DNA MassArray™ Automated Process Line, Press Release: Sep. 28, 1998, http://www.sequenom.com/pressrelease/92898.html.

Sequenom Uses DNA MassArray™ to Sequence Section of Human Cancer–Related p53 Gene, Press Release: Mar. 27, 1998, http://www.sequenom.com/pressreleases/32798.html.

Sequenom Reports DNA MassArray™ Technology More Sensitive Than Electrophoretic Methods in Detecting Gene Mutations, Press Release: Dec. 15, 1997, http://www.sequenom.com/pressrelease.htm.

Burlingame et al. "Mass Spectrometry," *Analytical Chemistry* 70:647R–716R (1998).

Crain et al. "Applications of mass spectrometry to the characterization of oligonucleotides and nucleic acids," *Current Opinion in Biotechnology* 9: 25–34 (1998).

Database CIN bie STN; AN(27)31:35339Bzu: "Mass spectrometry used to find mass of large intact nucleic acids," *Chem. Eng. News*. Jul. 13, 1998 (199980713) 76(28): p.55.

Eckerson et al. "Analysis of Proteins by Direct–Scanning Infrared–MALDI Mass Spectrometry after 2D–PAGE Separation and Electroblotting," *Anal. Chem.* 69: 2888–2892 (1997).

Good et al. "Antisense inhibition of gene expression in bacteria by PNA targeted to mRNA," *Nature Biotechnology* 16: 355–8 (1998).

Good et al. "Inhibition of translation and bacterial growth by peptide nucleic acid targeted to ribosomal RNA," *Proc. Natl. Acad. Sci. USA* 95: 2073–6 (1998).

Good et al. "Review: Progress in Developing PNA as a Gene–Targeted Drug," *Antisense & Nucleic Acid Drug Development* 7: 431–7 (1997).

Griffin et al. "Genetic analysis by peptide nucleic acid affinity MALDI–TOF mass spectrometry," *Nature Biotechnology* 15: 1368–72 (1997).

Hyrup, B. and P.E. Nielsen, "Review Article: Peptide Nucleic Acids (PNA): Synthesis, Properties, and Potenial Applications," *Bioorganic & Medicinal Chemistry* 4(1): 5–23 (1996).

Jiang–Baucom et al. "DNA Typing of Human Leukocyte Antigen Sequence Polymorphisms Nucleic Acid Probes and MALDI–TOF Mass Spectrometry," *Analytical Chemistry* 69: 4894–8 (1997).

Karas et al. "Matrix Dependence of Metastable Fragmentation of Glycoproteins in MALDI TOF Mass Spectrometry," *Anal. Chem.* 67: 675–679 (1995).

Nielsen et al. "Sequence–Selective Recognition of DNA by Strand Displacement with a Thymine–Substituted Polyamide," *Science* 254: 1497–1500 (1991).

Hahner et al. Matrix–Assisted Laser Desorption/Ionization Mass Spectrometry (MALDI) of Endonuclease Digests of RNA, *Nucleic Acid Research*, v. 25, 10:1957–1964 (1997).

Nordoff E., Matrix–Assisted Laser Desorption/Ionization Mass Spectrometry as a new method for the characterization of nucleic acids, *Trac, Trends in Analytical Chemistry, GB, Analytical Chemistry*, v. 15, 6:240–250 (1996).

Overberg et al., Matrix–Assisted Laser Desorption Mass Spectrometry: A Sensitive Technique for the Analysis of Macromolecules, *Laser und Optoelectronik Fuer Markomolekuele*, v. 24, 1:50–58 (1992).

Clark et al., Experimenting in picoliter microvials, *CHEMTECH* 28:20–25 (1998).

Spengler et al., Fundamental aspects of postsource decay in matrix–assisted laser desorption mass spectrometry, *J. Phys. Chem.* 96:9678–9684 (1992).

Gruic–Sovolj et al., Detection of noncovalent tRNA–aminoacyl–tRNA synthetase complexes by matrix–assisted laser desorption/ionization mass spectrometry, *J. of Biol. Chem.* 1997, 272, 32084–91.

*Protein LabFax*, ed., N.C. Price; Bios Scientific Publ. pp. 273–276 (1996).

Vestal et al., Delayed extraction matrix–assisted laser desorption time–of–flight mass spectrometry, *Rapid Commun. Mass Spectrom.* 9:1044–1050 (1995).

Ferstenau and Benner, Molecular weight determination of megadalton DNA electrospray ions using charge detection time–of–flight mass spectrometry, *Rapid Commun. Mass Spectrom.* 9:1528–1538 (1995).

McLaffery et al., High–resolution tandem FT mass spectrometry above 10 kDa, *Acc. Chem. Res.* 27:297–386 (1994).

Ross and Belgrader, Analysis of short tandem repeat polymorphisms in human DNA by matrix–asisted laser desorption/ionization mass spectrometry, *Anal. Chem.* 69:3966–3972 (1997).

IR-MALDI MASS SPECTROMETRY OF NUCLEIC ACIDS USING LIQUID MATRICES

RELATED APPLICATIONS

This application is a continuation of U.S. application Ser. No. 09/074,936, filed May 7, 1998, to Franz Hillenkamp, entitled "IR-MALDI Mass Spectrometry of Nucleic Acids Using Liquid Matrices." The subject matter this application is herein incorporated by reference in its entirety.

1. BACKGROUND OF THE INVENTION

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For molecules of low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented, forming secondary ions by the so-called collision induced dissociation (CID). The fragmentation pattern/pathway very often allows the derivation of detailed structural information.

During the last decade, mass spectrometry (MS) has become an important analytical tool in the analysis of biological macromolecules. This is due at least in part to introduction of the so-called "soft ionization" methods, namely Matrix-Assisted Laser Desorption/Ionization (MALDI) and ElectroSpray Ionization (ESI), which allow intact ionization, detection and exact mass determination of large molecules, i.e. well exceeding 300 kDa in mass (Fenn, J. B., et al., (1989) *Science* 246, 64–71; Karas M. & Hillenkamp F. (1988) *Anal. Chem.* 60, 2299–3001).

MALDI-MS (reviewed in (Nordhoff E., et al., (1997) *Mass Spectrom. Rev.* 15: 67–138.) and ESI-MS have been used to analyze nucleic acids. However, since nucleic acids are very polar biomolecules, that are difficult to volatilize, there has been an upper mass limit for clear and accurate resolution. ESI would seem to be superior to MALDI for the intact desorption of large nucleic acids even in the MDa mass range (Fuerstenau S. D. & Benner W. H. (1995). *Rapid Commun. Mass Spectrom.* 9, 15281–38; Chen R., Cheng X., Mitchell et al., (1995). *Anal. Chem.* 67, 1159–1163.). However, mass assignment is very poor and only possible with an uncertainty of around 10%. The largest nucleic acids that have been accurately mass determined by ESI-MS, so far, are a 114 base pair double stranded PCR product (Muddiman D.C., Wunschel D. S., Lis C., Pasâ-Tolic L., Fox K. F., Fox A., Anderson G. A. & Smith R. D. (1996) *Anal. Chem.* 68, 3705–3712) of about 65 kDa in mass and a 120 nucleotide *E. coli* 5S rRNA of about 39 kDa in mass (Limbach, P. A. Crain, P. F., McCloskey, J. A., (1995) *J. Am. Soc. Mass Spectrom.* 6:27–39.). ESI furthermore requires extensive sample purification. A few reports on the MALDI-MS of large DNA molecules with lasers emitting in the ultraviolet (UV) have been reported (Ross P. L. & P. Belgrader (1997) *Anal. Chem.* 69: 3966–3972; Tang K., et al., (1994) *Rapid Commun. Mass Spectrum.* 8: 727–730; Bai J., et al., (1995) *Rapid Commun. Mass Spectrum.* 9: 1172–1176; Liu Y-H., et al., (1995) *Anal. Chem.* 67: 3482–3490 and Siegert C. W., et al., (1997) *Anal. Biochem.* 243, 55–65. However, based on these reports it is clear that analysis of nucleic acids exceeding 30 kDa in mass (i.e. ca. a 100mer) by UV-MALDI-MS gets increasingly difficult with a current upper mass limit of about 90 kDa (Ross P. L. & P. Belgrader (1997) *Anal. Chem.* 69: 3966–3972). The inferior quality of the DNA UV-MALDI-spectra has been attributed to a combination of ion fragmentation and multiple salt formation of the phosphate backbone. Since RNA is considerably more stable than DNA under UV-MALDI conditions, the accessible mass range for RNA is up to about 150 kDa (Kirpekar F., et al., (1994). *Nucleic Acids Res.* 22, 3866–3870). The analysis of nucleic acids by IR-MALDI with solid matrices (mostly succinic acid and, to a lesser extent, urea and nicotinic acid) has been described (Nordhoff, E. et al., (1992) *Rapid Commun. Mass Spectrom.* 6: 771–776; Nordhoff, E. et al., (1993) *Nucleic Acids Res.* 21: 3347–3357; and Nordhoff, E. et al., (1995) *J. Mass Spec.* 30: 99–112). The 1992 Nordhoff et al., paper reports that a 20-mer of DNA and an 80-mer of RNA were about the uppermost limit for resolution. The 1993 Nordhoff et al. paper, however, provides a distinct spectra for a 26-mer of DNA and a 104-mer of tRNA. The 1995 Nordhoff et al., paper shows a substantially better spectra for the analysis of a 40-mer by UV-MALDI with the solid matrix, 3-hydroxy picolinic acid, than by IR-MALDI with succinic acid (See FIGS. 1(d) and 1(e)). In fact the 1995 paper reports that IR-MALDI resulted in a substantial degree of prompt fragmentation.

Nucleic acid analysis can be useful, for example, for diagnosing the existence of a genetic disease or chromosomal abnormality; a predisposition to a disease or condition, infection by a pathogenic organism or to provide information relating to identity, heredity or compatibility. Since mass spectrometry can be performed relatively quickly and is amenable to automation, improved methods for obtaining accurate mass spectra for larger nucleic acid molecules (e.g. larger than about 90 kDa of DNA and 150 kDa of RNA) are clearly needed.

2. SUMMARY OF THE INVENTION

In one aspect, the invention features processes for rapidly and accurately determining the mass of nucleic acids (e.g. DNA or RNA) using infrared matrix assisted laser desorption ionization (IR-MALDI) mass spectrometry and a liquid matrix.

In a preferred embodiment, a solution containing the nucleic acid and a liquid matrix is deposited onto a substrate to form a homogeneous, transparent thin layer of nucleic acid solution, which is then illuminated with infrared radiation, so that the nucleic acid is desorbed and ionized, thereby emitting ion particles, which are then analyzed using a mass analyzer to determine the identity of the nucleic acid. Preferably, sample preparation and deposition is performed using an automated device.

Preferred liquid matrices for use herein have a sufficient absorption at the wavelength of the laser to be used in performing desorption and ionization and are a liquid (not a solid or a gas) at room temperature (20° C.). For absorption purposes, the liquid matrix can contain at least one chromophore or functional group that strongly absorbs infrared radiation. Preferred functional groups include: nitro, sulfonyl, sulfonic acid, sulfonamide, nitrile or cyanide, carbonyl, aldehyde, carboxylic acid, amide, ester, anhydride, ketone, amine, hydroxyl, aromatic rings, dienes and other conjugated systems.

Particularly preferred liquid matrices are substituted or unsubstituted: (1) alcohols, including: glycerol, 1,2- or 1,3-propane diol, 1,2-, 1,3- or 1,4-butane diol, triethanolamine;

(2) carboxylic acids including: formic acid, lactic acid, acetic acid, propionic acid, butanoic acid, pentanoic acid, hexanoic acid and esters thereof; (3) primary or secondary amides including acetamide, propanamide, butanamide, pentanamide and hexanamide, whether branched or unbranched; (4) primary or secondary amines, including propylamine, butylamine, pentylamine, hexylamine, heptylamine, diethylamine and dipropylamine; (5) nitrites, hydrazine and hydrazide.

Preferably, a liquid matrix for use herein, is miscible with a nucleic acid compatible solvent. It is also preferable that the liquid matrix is vacuum stable, i.e. has a low vapor pressure, so that the sample does not evaporate quickly in the mass analyzer. Preferably the liquid should also be of an appropriate viscosity to facilitate dispensing of micro- to nano-liter volumes of matrix alone or mixed with a nucleic acid compatible solvent. Mixtures of different liquid matrices and additives to such matrices may be desirable to confer one or more of the above-described properties.

Once prepared, the nucleic acid/matrix solution is deposited as a thin layer on a substrate, which is preferably contained within a vacuum chamber. Preferred substrates for holding the nucleic acid/matrix solution are selected from the group consisting of: beads, capillaries, flat supports, pins and wafers, with or without filter plates. Preferably the temperature of the substrate can be regulated to cool the nucleic acid/matrix solution to a temperature that is below room temperature.

Preferred infrared radiation is in the mid-IR wavelength region from about 2.5 µm to about 12 µm. Particularly preferred sources of radiation include CO, $CO_2$ and Er lasers. In certain embodiments, the laser can be an optic fiber or the laser radiation can be coupled to the mass spectrometer by fiber optics.

In a further preferred embodiment, the ion particles generated from the analyte are extracted for analysis by the mass analyzer in a delayed fashion prior to separation and detection in a mass analyzer. Preferred separation formats include linear or reflector (with linear and nonlinear fields, e.g. curved field reflectron) time-of-flight (TOF), single or multiple quadrupole, single or multiple magnetic sector, Fourier transform ion cyclotron resonance (FTICR) or ion trap mass spectrometers.

Using the processes reported herein, accurate (i.e at least about 1% accurate) masses of sample DNA can be obtained for at least about 2000-mers of DNA (i.e. masses of at least about 650 kDa) and at least about 1200-mers of RNA (i.e. masses of at least about 400 kDa). In addition, signals of single stranded as well as double stranded nucleic acids can be obtained in the spectra.

The improved accuracy for measuring the mass of deoxyribonucleic acids (DNA) by IR-MALDI mass spectrometry (accuracy of at least about 1%) is far superior to that provided by standard agarose gel sizing of nucleic acids (accuracy of about 5%). Mass determination of ribonucleic acids (RNA) by IR-MALDI mass spectrometry (accuracy of at least about 0.5%) is even more significant, since an accurate size determination of RNA by gel analysis is difficult if not impossible, in part because of the absence of suitable size markers and of a really well-suited gel matrix.

As important as the extension in mass range is the dramatic decrease in the amount of analyte needed for preparation, down to the low femtomole (fmol) and even the attomole (amol) range even with an essentially simple preparation method. In addition, by using a liquid rather than a solid matrix, the ion signals generated have been found to be more reproducible from shot to shot. Use of a liquid matrix also facilitates sample dispensation, for example to various fields of a chip array. Further, by using a liquid matrix in conjunction with IR-MALDI mass spectrometry, essentially all sample left on the target after IR-MALDI analysis can be retrieved for further use.

Other features and advantages of the invention will be apparent from the following detailed description and claims.

3. BRIEF DESCRIPTION OF THE FIGURES

FIG. 1 shows the following mass spectra of a synthetic DNA 70-mer: FIG. 1(*a*) ultraviolet matrix assisted laser desorption ionization (UV-MALDI) and detection by a linear time-of-flight (TOF) instrument using delayed extraction and a 3 hydroxypicolinic acid (3HPA) matrix (sum of 20 single shot mass spectra); FIG. 1(*b*) UV-MALDI-reflectron (ret) TOF spectrum, using delayed extraction and a 3HPA matrix (sum of 25 single shot mass spectra); and FIG. 1(*c*) IR-MALDI-retTOF spectrum, using delayed extraction and a glycerol matrix, (sum of 15 single shot mass spectra).

FIG. 2 shows the following IR-MALDI RetTOF mass spectra using a 2.94 µm wavelength and a glycerol matrix: FIG. 2(*a*) a synthetic DNA 21 mer (sum of 10 single shot spectra); FIG. 2(*b*) a DNA mixture comprising a restriction enzyme products of a 280mer (87 kDa), a 360mer (112 kDa), a 920mer (285 kDa) and a 1400mer (433 kDa) (sum of 10 single shot spectra); FIG. 2(*c*) DNA mixture; restriction enzyme products of a 130mer (ca. 40 kDa), a 640mer (198 kDa) and a 2180mer (674 kDa) (sum of 20 single shot spectra); and (*d*) an RNA 1206mer (ca.387 kDa), (sum of 15 single shot spectra). Ordinate scaling is intercomparable.

Figure 3A:
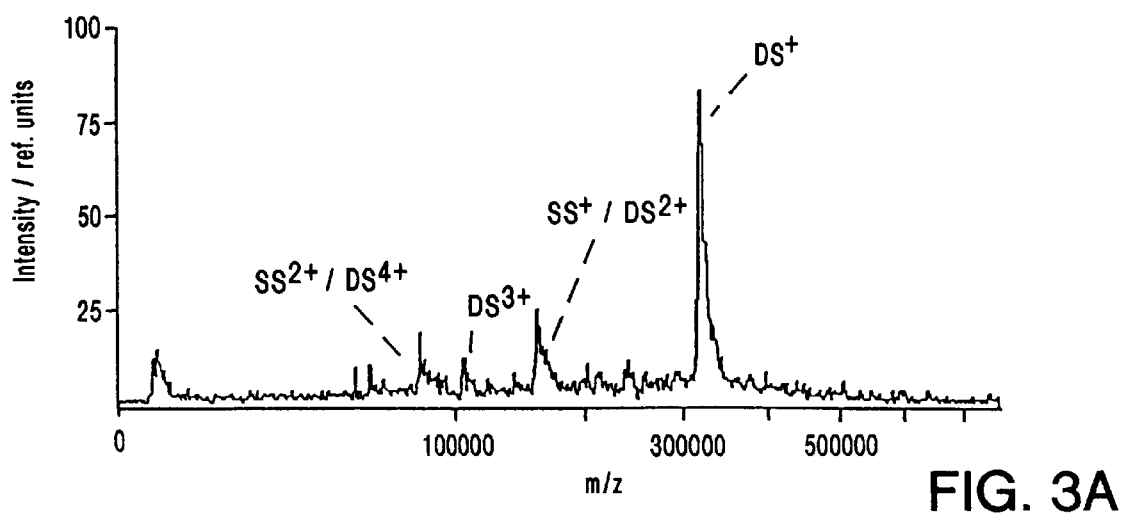

FIG. 3 shows the spectra of a 515-mer double stranded PCR DNA product. The following different total amounts of sample were loaded: 3(*a*) 300 fmol, single shot spectrum; 3(*b*) 3 fmol, sum of single shot spectra; 3(*c*) 300 amol, sum of 25 single shot spectra obtained using an IR-MALDI RetTOF, wherein the laser emitted at a wavelength of 2.94 µm using a glycerol matrix.

4. DETAILED DESCRIPTION OF THE INVENTION

The instant invention is based, at least in part, on the surprising finding that high resolution mass spectra of large nucleic acid molecules (DNA and RNA) can be obtained by desorbing and ionizing the nucleic acids in a liquid matrix using a laser that emits in the infrared electromagnetic wavelength.

The invention therefore features a process for performing matrix assisted laser desorption ionization (MALDI) mass spectrometry, comprising mixing a nucleic acid solution with a liquid matrix to form a matrix/nucleic acid solution and depositing the solution onto a substrate to form a homogeneous, thin layer of matrix/nucleic acid solution. The nucleic acid containing substrate can then be illuminated with infrared radiation of an appropriate wavelength to be absorbed by the matrix, so that the nucleic acid is desorbed and ionized, thereby emitting ion particles that can be extracted (separated) and analyzed by a mass analyzer to determine the mass of the nucleic acid.

Nucleic acids to be analyzed according to the processes of the invention can include any single stranded or double stranded polynucleotide, such as deoxyribonucleic acid (DNA), including genomic or cDNA, ribonucleic acid (RNA) or an analog of RNA or DNA, as well as nucleotides or nucleosides and any derivative thereof. Nucleic acids can be of any size ranging from single nucleotides or nucleosides to tens of thousands of base pairs (-mers). For analysis herein, preferred nucleic acids are thousand-mers or less.

Nucleic acids may be obtained from a "biological sample" (i.e. any material obtained from any living source (e.g. human, animal, plant, bacteria, fungi, protist, virus) using any of a number of procedures, which are well-known in the art. The particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acids from blood (Rolff, A et al., PCR: Clinical Diagnostics and Research, Springer (1994)). Prior to being mixed with a liquid matrix, the particular nucleic acid may require further processing to yield a relatively pure nucleic acid sample. For example, a standard ethanol precipitation may be performed on restriction enzyme digested DNA. Alternatively, PCR products may require primer removal prior to analysis. Likewise, RNA strands can be separated from the molar excess of premature termination products always present in in vitro transcription reactions.

As used herein, the term "liquid matrix" is meant to refer to a matrix that has a sufficient absorption at the wavelength of the laser to be used in performing desorption and ionization and that is a liquid (not a solid or a gas) at room temperature (about 20° C.).

For absorption purposes, the liquid matrix can contain at least one chromophore or functional group that strongly absorbs infrared radiation. Examples of appropriate functional groups include: nitro, sulfonyl, sulfonic acid, sulfonamide, nitrile or cyanide, carbonyl, aldehyde, carboxylic acid, amide, ester, anhydride, ketone, amine, hydroxyl, aromatic rings, dienes and other conjugated systems.

Preferred liquid matrices are substituted or unsubstituted: (1) alcohols, including: glycerol, 1,2- or 1,3-propane diol, 1,2-, 1,3- or 1,4-butane diol, triethanolamine; (2) carboxylic acids including: formic acid, lactic acid, acetic acid, propionic acid, butanoic acid, pentanoic acid, hexanoic acid and esters thereof; (3) primary or secondary amides including acetamide, propanamide, butanamide, pentanamide and hexanamide, whether branched or unbranched; (4) primary or secondary amines, including propylamine, butylamine, pentylamine, hexylamine, heptylamine, diethylamine and dipropylamine; (5) nitrites, hydrazine and hydrazide. Particularly preferred compounds are comprised of eight or fewer carbon atoms. For example, particularly preferred carboxylic acids and amides are comprised of six or fewer carbon atoms, preferred amines are comprised of about three to about seven carbons and preferred nitrites are comprised of eight or fewer carbons. However, compounds that are unsaturated to any degree may be comprised of a larger number of carbons, since unsaturation confers liquid properties on a compound. Although the particular compound used as a liquid matrix must contain a functional group, the matrix is preferably not so reactive that it may fragment or otherwise damage the nucleic acid to be analyzed.

An appropriate liquid should also be miscible with a nucleic acid compatible solvent. Preferably the liquid should also be of an appropriate viscosity, e.g. typically less than or equal to about 1.5 $Ns/m^2$, (the viscosity of glycerol at room temperature) to facilitate dispensing of micro- to nano-liter volumes of matrix alone or mixed with a nucleic acid compatible solvent. For use herein, a liquid matrix should also have an appropriate survival time in the vacuum of the analyzer (typically having a pressure in the range of about $10^{-5}$ to about $10^{-10}$ mbars) to allow the analysis to be completed. Liquids having an appropriate survival time are "vacuum stable", a property, which is strictly a function of the vapor pressure of the matrix, which in turn is strongly dependent on the sample temperature. Preferred matrices have a low vapor pressure at room temperature, so that less than about fifty percent of the sample in a mass analyzer having a back pressure, which is less than or equal to $10^{-5}$ mbars, evaporates in the time needed for the analysis of all samples introduced (e.g. from about 10 min to about 2 hrs.). For example, for a single sample, the analysis may be performed in minutes. However, for multiple samples, the analysis may require hours for completion. For example, glycerol can be used as a matrix at room temperature in a vacuum for about 10 to 15 minutes. However, if glycerol is to be used for analyzing multiple samples in a single vacuum, the vacuum may need to be cooled to maintain the sample at a temperature, which is in the range of about −50° C. to about −100° C. (173 K to about 223K) for the time required to complete the analysis. Triethanolamine, in contrast, has a much lower vapor pressure than glycerol and can survive in a vacuum for at least about one hour even at room temperature.

Mixtures of different liquid matrices and additives to such matrices may be desirable to confer one or more of the above-described properties. For example, an appropriate liquid matrix could be comprised of a small amount of an IR chromophore containing solution and a greater amount of an IR invisible (i.e. nonabsorbing) material, in which, for example, the nucleic acid is soluble. It may also be useful to use a matrix, which is "doped" with a small amount of a compound or compounds having a high extinction coefficient (E) at the laser wavelength used for desorption and ionization, e.g. dinitrobenzenes, polyenes, etc. An additive that acidifies the liquid matrix may also be added to dissociate double stranded nucleic acids or to denature secondary structures of nucleic acids, such as that of t-RNA. Additional additives may be useful for minimizing salt formation between the matrix and the phosphate backbone of the nucleic acid. For example, the additive can comprise an ammonium salt or ammonium-loaded ion exchange bead, which removes alkali ions from the matrix. Alternatively, the liquid matrix can be distilled prior to mixture with the nucleic acid solution, to minimize salt formation between the matrix and the phosphate backbone of the nucleic acid. The liquid matrix can also be mixed with an appropriate volume of water or other liquid to control sample viscosity and rate of evaporation. Since literally all of the water is evaporated during mass analysis, an easily manipulated volume (e.g. 1 $\mu$l) can be used for sample preparation and transfer, but still result in a very small volume of liquid matrix. As a result, only small volumes of nucleic acid are required to yield about $10^{-16}$ moles to about $10^{-12}$ moles (about 100 attomoles to about 1 picomole) of nucleic acid in the final liquid matrix droplet.

As shown in the following examples, when glycerol is used as a matrix, the final analyte-to-glycerol molar ratio (concentration) should be in the range of about $10^{-4}$ to $10^{-9}$ depending on the mass of the nucleic acid and the total amount of nucleic acid available. For example, for the sensitivity test described in the following examples, the relatively high concentration of nucleic acid used was measured by standard UV-spectrophotometry. Practically speaking, one typically knows the approximate amount of nucleic acid generated, e.g. from a PCR or transcription reaction. The large range specified indicates that the actual amount of nucleic acid analyzed is not very critical. Typically, a greater amount of nucleic acid results in a better spectra. However, there may be instances where the nucleic acid sample requires dilution.

Preferably, nucleic acid samples are prepared and deposited as a thin layer (e.g. a monolayer to about a 100 μm layer, preferably between about 1 μm to 10 μm) onto a substrate using an automated device, so that multiple samples can be prepared and analyzed on a single sample support plate with only one transfer into the vacuum of the analyzer and requiring only a relatively short period of time for analysis. Appropriate automated sample handling systems for use in the instant process are described, for example, in U.S. Pat. Nos. 5,705,813, 5,716,825 and 5,498,545. Any substrate on which the nucleic acid/liquid matrix can be deposited and retained for desorption and ionization of the nucleic acid can be used in the process of the instant invention. Preferred substrates are beads (e.g. silica gel, controlled pore glass, magnetic, Sephadex/Sepharose, cellulose), capillaries, flat supports (e.g. filters, plates or membranes made of glass, metal surfaces (steel, gold, silver, aluminum, copper or silicon) or plastic (e.g. polyethylene, polypropylene, polyamide, polyvinylidenefluoride), pins (e.g. arrays of pins suitable for combinatorial synthesis or analysis of beads in pits of flat surfaces such as wafers, with or without filter plates).

The sample containing substrate can then be analyzed in a vacuum chamber of a mass analyzer to identify the nucleic acid. Preferably, the mass analyzer can maintain the temperature of a sample at a preselected value, e.g. a temperature in the range of at least about −100° C. to about 80° C., during sample preparation, disposition or analysis. For example, improved spectra may be obtained, in some instances, by cooling the sample to a temperature below room temperature (i.e. below 20° C.) during sample preparation and/or mass analysis. Further, as described above, the vacuum stability of a matrix may be increased by cooling. Alternatively, it may be useful to heat a sample to denature double stranded nucleic acids into single strands or to decrease the viscosity during sample preparation.

Desorption and ionization of the sample is then performed in the mass analyzer using infrared radiation. "Infrared radiation" or "infrared wavelength" refers to electromagnetic wavelengths, which are longer than those of red light in the visible spectrum and shorter than radar waves. Preferred infrared wavelengths for use in the instant invention are in the mid-IR wavelength region (i.e. from about 2.5 μm to about 12 μm). Preferred sources of infrared radiation are CO lasers, which emit at about 6 μm, $CO_2$ lasers, which emit at about 9.2–11 μ, Er lasers with any of a variety of crystals (e.g. YAG or YILF) emitting at wavelengths around 3 μm and optical paramagnetic oscillator lasers emitting in the range of about 2.5 μm to about 12 μm The pulse duration and/or size of the irradiated area (spot size) can be varied to generate multiple charged ions. A preferred pulse duration is in the range of about 100 picoseconds (ps) to about 500 nanoseconds (ns). A preferred spot size is in the range of about 50 μm in diameter to about 1 mm.

IR-MALDI can be matched with an appropriate mass analyzer, including linear (lin) or reflector (ret) (with linear and nonlinear fields, e.g. curved field reflectron) time-of-flight (TOF), single or multiple quadrupole, single or multiple magnetic sector, Fourier transform ion cyclotron resonance (FTICR) or ion trap. Preferably detection is performed using a linear or reflectron mode TOF instrument in positive or negative ion mode, so that the ions are accelerated through a total potential difference of about 3–30 kV in the split extraction source using either static or delayed ion extraction (DE). Time-of-flight (TOF) mass spectrometers separate ions according to their mass-to-charge ratio by measuring the time it takes generated ions to travel to a detector. The technology behind TOF mass spectrometers is described for example in U.S. Pat. Nos. 5,627,369, 5,625,184, 5,498,545, 5,160,840 and 5,045, 694, the teachings of which are each specifically incorporated herein by reference.

Delayed extraction with delay times ranging from about 50 ns to about 5 μs may improve the mass resolution of some nucleic acids (e.g. nucleic acids in the mass range of from about 30 kDa to about 50 kDa using either a liquid or solid matrix).

The improved processes for detecting nucleic acids by mass spectrometry can be useful, for example, for diagnosing the existence of any one of the more than 3000 known genetic diseases (Human Genome Mutations, D. N. Cooper and M. Krawczak, BIOS Publishers, 1993) including hemophilias, thalassemias, Duchenne Muscular Dystrophy (DMD), Huntington's Disease (HD), Alzheimer's Disease and Cystic Fibrosis (CF) or genetic diseases to be identified. In addition, the processes can be useful for diagnosing certain birth defects, which are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Kleinfelter's Syndrome (XXY). The processes can also be used to detect certain DNA sequences that may predispose an individual to any of a number of diseases, such as diabetes, arteriosclerosis, obesity, various autoimmune diseases and cancer (e.g. colorectal, breast, ovarian, prostate, lung) or that render an individual suitable or unsuitable for a particular medical treatment.

Alternatively, the processes can be used to detect nucleic acids that are characteristic of viruses, bacteria, fungi and other infectious organisms, which are different from the sequences contained in the host cell. Finally, the processes can be used to detect characteristic nucleic acid sequences that provide information relating to identity, heredity or compatibility.

Examples of disease causing viruses that infect humans and animals and which may be detected by the disclosed processes include: Retroviridae (e.g., human immunodeficiency viruses, such as HIV-1 (also referred to as HTLV-III, LAV or HTLV-III/LAV, See Ratner, L. et al., *Nature*, Vol. 313, Pp. 227–284 (1985); Wain Hobson, S. et al., *Cell*, Vol. 40: Pp. 9–17 (1985)); HIV-2 (See Guyader et al., *Nature*, Vol. 328, Pp. 662–669 (1987); European Patent Application No. 0 269 520; Chakraborti et al., *Nature*, Vol. 328, Pp. 543–547 (1987); and European Patent Application No. 0 655 501); and other isolates, such as HIV-LP (International Publication No. WO 94/00562 entitled "A Novel Human Immunodeficiency Virus"; Picornaviridae (e.g., polio viruses, hepatitis A virus, (Gust, I. D., et al., *Intervirology*, Vol. 20, Pp. 1–7 (1983); entero viruses, human coxasackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g. coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parentally transmitted (i.e., Hepatitis C); Norwalk and related viruses, astroviruses).

Examples of infectious bacteria include: *Helicobacter pyloris, Borelia burgdorferi, Legionella pneumophilia,* Mycobacteria sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus antracis, corynebacterium diphtheriae*, corynebacterium sp., *Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue*, Leptospira, and *Actinomyces isrealli.*

Examples of infectious fungi include: *Cryptococcus neoformans, Histoplasma capsulatum, Coccidioides immitis, Blastomyces dermatidis, Chlamydia trachomatis, Candida albicans*. Other infectious organisms (i.e., protists) include: *Plasmodium falciparum* and *Tocxoplasma gondii.* The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); B. Perbal, *A Practical Guide To Molecular Cloning* (1984); the treatise, *Methods In Enzymology* (Academic Press, Inc., N.Y.).

EXAMPLE 1

MALDI Mass Spectrometry of Nucleic Acids Ranging From a 70-mer to a 2180-mer

Materials and Methods

Samples

Synthetic oligodeoxynucleotides were obtained from Pharmacia Biotech (Uppsala, Sweden). The 70-mer was FPLC-purified by the supplier, while the smaller ones were used without additional purification. Plasmid DNA was purified from the *E. coli* strain DH5a by use of the Qiagen midiprep kit (QIAGEN GmbH, Hilden, Germany) according to the manufactures recommendations. Restriction enzymes were obtained from New England Biolabs GmbH (Schwalbach/Taunus, Germany); restriction enzyme digests of plasmid DNA were performed according to the supplier's protocols. Samples intended for MALDI-MS analysis were adjusted to 10 mM EDTA and 2 M $NH_4$-acetate, and precipitated with 2 volumes of ethanol. The pellet was washed once with 70% ethanol and dissolved in water to an approximate concentration of 0.5 pmol/$\mu$L.

The 1206 nucleotide in vitro transcript was synthesized and ethanol precipitated according to standard procedures (Kirkepar, F. et al., (1994) *Nucleic Acids Res.* 22: 3866–3870), using the restriction enzyme Scal digested plasmid pBluescript KS+ as template for the T3 RNA polymerase (MBI Fermentas, Vilnius, Lithuania). A 10 $\mu$L Poros 50 R2 (PerSeptive Biosystems, Framingham, Mass.) reverse phase column was prepared and equilibrated with 3% acetonitrile/10 mM triethyl ammoniumacetate (TEAA) as described elsewhere (Kussman, M. et al., (1997) *J. Mass. Spectrom.* 32: 593–6010. The RNA sample was adjusted to 0.3 M TEAA and loaded onto the column. The column was washed with 200 $\mu$L 3% acetonitrile/10 mM TEAA, and the sample was eluted with 10 uL 25% acetonitrile/10 mM TEAA. Subsequent to lyophillization, the eluate was dissolved in 5 $\mu$L water; the estimated sample concentration was 1 pmol/$\mu$L.

A crude DNA preparation from mycoplasma-infected HELA cells was made, and a PCR performed essentially as described (Hopert, A. et al., (1993) *J. Immunol. Methods* 164: 91–100) using the primers 5'-CGC CTG AGT AGT ACG TTC GC-3' (SEQ ID NO. 1) and 5'-GCG GTG TGT ACA AGA CCC GA-3' (SEQ ID NO. 2), and recombinant Taq DNA polymerase (MBI Fermentas, Vilnius, Lithuania). The PCR results in an approximate 515 bp DNA fragment originating from the 16S rRNA gene of mycoplasma (Hopert, A. et al., (1993) *J. Immunol. Methods* 164: 91–100); the precise length of the PCR product cannot be predicted because the species of the mycoplasma is unknown. A reamplification by PCR was performed under identical conditions using the same primer set, and the final product was adjusted to 4 mM EDTA/2M $NH_4$-acetate, and precipitated as described for the restriction enzyme digests. The pellet was dissolved in 200 $\mu$L water and purified over a Microcon-100 (Amicon GmbH, Witten, Germany) microconcentrator, by three successive diafiltrations with 100 $\mu$L water as recommended by the manufacturer. The retenate was lyophilized and re-dissolved in water to a concentration of 0.6 pmol/$\mu$L as determined by UV spectrophotometry.

Sample Preparation

For IR-MALDI, glycerol was used as the matrix. The glycerol was incubated with an equal volume of a $H^+$-cation exchange bead suspension (Dowex 50W-X8. Biorad AG, Munich, Germany) in order to reduce subsequent alkali salt formation of the nucleic acid backbone phosphates. Typically 0.5–1 $\mu$L of glycerol were mixed with an equal amount of an aqueous analyte solution on the target to give a final analyte-to-glycerol molar ratio of the sample of about $10^{-4}$–$10^{-7}$, depending, on the mass of the analyte. The mixture was smeared out evenly over an area of ca.1–2 $mm^2$ to form a homogeneous, transparent thin layer on the stainless steel substrate. The water was evaporated off at a pressure of typically $10^{-2-1}$ Pa, before sample introduction into the mass spectrometer.

Samples for UV-MALDI-MS were prepared by on-target mixing of 1 μL of a $10^{-5}$ to $10^{-6}$ M aqueous analyte solution with 0.7 μL of a 50 g/l 3-hydroxypicolinic acid (3HPA) solution in 20% acetonitrile. About ten ammonium-loaded cation exchange beads were added to the samples before drying in a cool stream of air (Nordshoff, E. et al., (1992) *Rapid Commun. Mass Spectrom.* 60: 771–776).

Instrumental

The experiments were carried out with an in-house built MALDI single stage reflectron time-of-flight (TOF) mass spectrometer of 3.5 m equivalent flight length (Berkenkamp, S. et al., (1997) *Rapid Commun. Mass Spectrom.* 11:1399–1406, which is set forth as Example 2). The mass spectrometer can also be used in the linear TOF mode. Unless specifically mentioned, the experiments reported here have been carried out in reflectron—and positive ion mode. Ions are accelerated through a total potential difference of about 16–25 kV in the split extraction source using either static or delayed ion extraction (DE). A Venetian blind secondary electron multiplier (EMI 9643) with a conversion dynode, mounted 10 mm in front of the cathode (ion impact energy of about 20–40 kV, depending on ion mass) or a Chevron Micro-Channel plate (Galileo Co., Sturbridge, Mass., USA) are used for ion detection. For high mass ions, the potential between the conversion dynode and the electron multiplier cathode is set to several thousand volts in order to increase the ion signal by making efficient use of the secondary ions. If maximum mass resolution is sought in the mass range up to several thousand Daltons, the potential between the two electrodes is kept below about 500 V in order to detect secondary electrons only and thereby avoid the time (and mass) dispersion of the secondary ions (see e.g. FIG. 2a). Signals are processed by a transient recorder with a time resolution of about 0.5 ns (LeCroy 9350). The digitized data are transferred to a PC for storage and further evaluation. For IR-MALDI experiments, an Er-YAG-Laser emitting at 2.94 μm (Spectrum GmbH, Berlin, Germany; τ=80–90 ns, energy stability ca. ±2–4% from shot to shot) was used. A frequency tripled Nd-YAG laser, emitting in the UV at 355 nm (τz=6 ns) was used for direct comparison between IR- and UV-MALDI. Single laser pulses are focused to a spot diameter of ca. 150 μm (IR) and 100 μm (UV) on the sample under an angle of 45°. Samples are observed in situ with a CCD camera of about 5 μm resolution.

Results

Figure 1B:
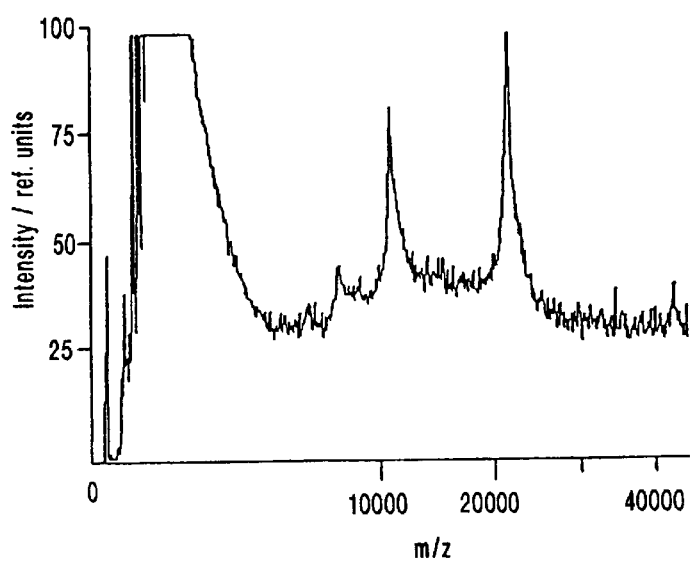
Figure 1C:
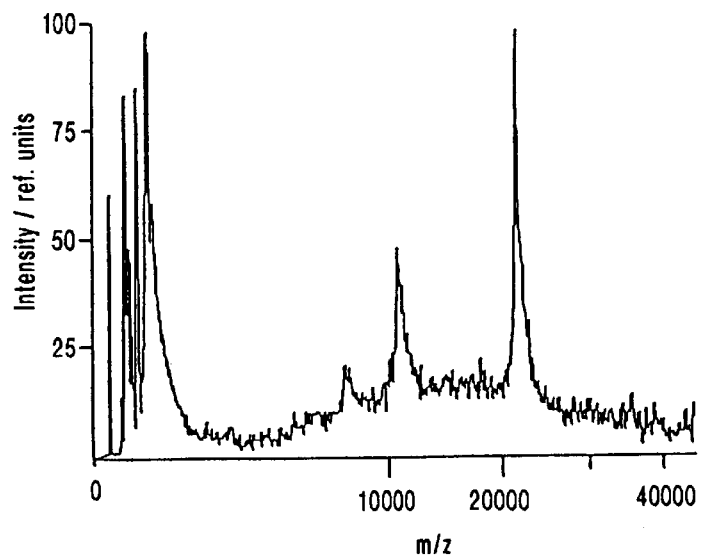

UV-MALDI spectra of DNA with at least about 50 nucleotides and with a reasonable quality could be obtained only in the linTOF, delayed-ion-extraction (DE) mode. FIGS. 1a and 1b demonstrate the striking differences in spectra quality for the two modes of operation for a synthetic DNA 70-mer (ca. 21.5 kDa) and a 3HPA matrix (355 nm). The quality of the spectrum of FIG. 1b, obtained in reflectron mode is quite inferior to that of FIG. 1a in several respects. Signal intensity as well as signal-to-noise ratio are considerably degraded as is the mass resolution, down to 15 (M/Δm; FWHM) from 65 in the spectrum of FIG. 1a. The saturated signal in the mass range below approximately 2000 Da in FIG. 2b reflects the increased laser fluence necessary to obtain analyte signals of the intensity shown. The loss in mass resolution is, for the most part, a result of the sloping low mass edge of the peaks, signaling abundant metastable small neutral losses. Exact mass determination is severely compromised by the loss of spectral quality. The IR-MALDI spectrum (refTOF, DE mode) of the same DNA 70-mer with glycerol as matrix is shown in FIG. 1c. The quality of this spectrum is comparable to UV-MALDI analysis obtained in the linear mode with respect to signal intensity and mass resolution (FIG. 1a). The base peak has a steeply rising low mass edge, demonstrating an essential absence of any metastable small neutral loss. This behavior was consistently observed for IR-MALDI of nucleic acid with glycerol as a matrix, qualifying it as a very gentle desorption method forming ions of nucleic acids of high ion stability. This contrasts strikingly to the IR-MALDI spectra of nucleic acids obtained with succinic acid as matrix (Nordhoff, E. et al., (1993) *Nucl. Acids Res.* 21: 3347–3357; FIGS. 1(d) and 1(c)). The absence of literally all metastable neutral loss for the glycerol matrix, therefore, was a very unexpected result not anticipated based on prior experience (See the Background of the Invention).

This leads to a broad mass range for the analysis of nucleic acids, from small oligonucleotides up to more than 2000 nt. as demonstrated in FIG. 2. A refTOF mass spectrum of a synthetic DNA 21-mer is shown in FIG. 2a. With delayed ion extraction a mass resolution of 1050 (FWHM) is obtained, comparable to the resolution obtained with the instrument for proteins in this mass range. Several poorly resolved peaks on the high mass side of the analyte peak appear in the spectrum. They are detection artifacts of residual secondary ions generated at the conversion dynode operated here in a mode to preferentially detect only secondary electrons in order to not degrade mass resolution by the ion detection system. FIG. 2b demonstrates the high mass range with a restriction enzyme digest of a plasmid (pBluescript-KS+ digested with BgII and RsaI), yielding four fragments of 280 bp, 360 bp, 920 bp, and 1,400 bp. All four signals represent single strands and are the composite signal of the two complementary strands. Very weak, if any signals of the double stranded oligomers are apparent in this spectrum. Tentatively, the dissociation of the double strands in samples prepared with purified glycerol is attributed to an acidification by the $H^+$ ion exchange resin. Not enough experience has, however, been accumulated so far to identify all additional parameters determining double strand dissociation under IR-MALDI conditions. The mass resolution of all high mass ion signals is about 50 (FWHM) and appears to be relatively independent of the ion mass. The IR-MALDI mass spectrum of FIG. 1c shows the upper mass limit measured so far for a restriction enzyme digest (130 bp, 640 bp, and 2,180 bp). The signal of the 2,180 nt ss-fragment was obtained only after heating the restriction digest to a temperature of 95° C. for 5 minutes. Such large DNA fragments apparently do not get separated into single strands under the conditions used, in contrast to the samples up to 1400 bp. The relatively poor mass resolution of ca. 30 for the 2,180 nt fragment in this spectrum and the strong background signals indicate an upper mass limit for IR-MALDI-MS of nucleic acids of approximately 700 kDa under the current conditions. Accordingly, the double stranded 2,180 nt fragment was not observable.

Figure 2A:
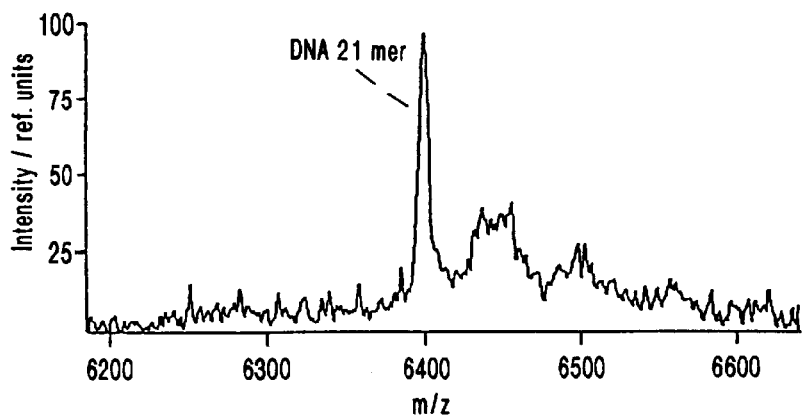
Figure 2B:
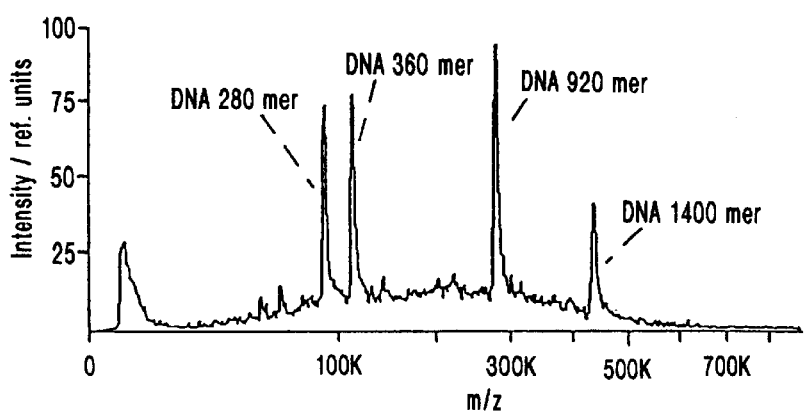
Figure 2C:
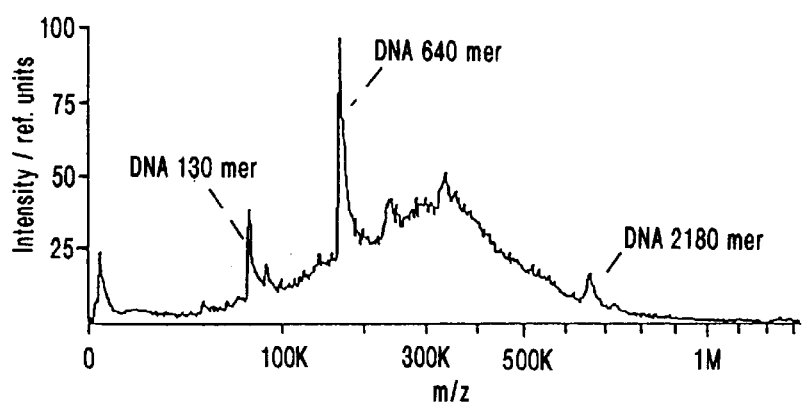
Figure 2D:
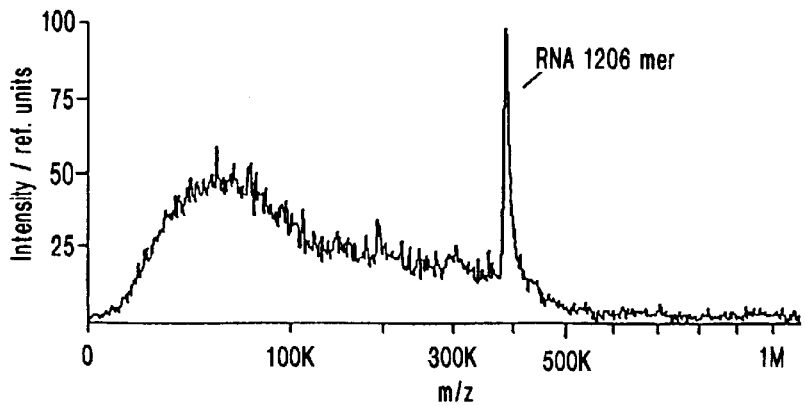

IR-MALDI-MS of large RNA is also possible as shown in FIG. 2d for an RNA 1206 nt in vitro transcript. The increased ion-stability for RNA compared to DNA, well documented for UV-MALDI, was not observed in IR-MALDI within the mass range tested in these experiments. Large DNA ions as well as large RNA appeared to be of comparable stability, stable enough even for TOF analysis in the reflectron mode. The large hump, centered at about 50 kDa is believed to reflect impurities of the sample rather than metastable fragments. The comparably steep rise of the peak at the low mass side also testifies to a very limited loss of small neutrals such as single bases.

One advantage of glycerol as matrix is the superior shot to shot reproducibility and mass precision (200–400 ppm)

(Nordhoff, E. et al., (1993) *Nucleic Acids Res.* 21: 3347–3357. These values, originally determined for proteins, are also valid for the analysis of smaller oligonucleotides. However, mass accuracy was found to be mass dependent. Using, an external 2 point calibration with angiotensin II (1047 Da) and bovine insulin (5743 Da) the mass of the 21 mer (6398 Da) in FIG. 2a was determined to within ±2 Da of the known mass, i.e. an accuracy of 0.03%. The molecular mass of the 70mer (theoretical mass: 21517 Da) was determined to within ±25 Da i.e. a mass accuracy of 0.1% from the spectrum of FIG. 1c, calibrated with cytochrome C oligomers. ($M^+$, $2M^+$, $3M^+$).

For all of the ten different samples of high mass DNA analyzed, the measured mass was within less than about 1% of the theoretical mass derived from the sequence (see e g. FIGS. 2b and 2c). The average mass of the two single strands was used as the theoretical mass in the case of DNA restriction enzyme fragments. The masses of the two single strands never differed by more than about 1%. Only one large mass RNA has been measured so far (FIG. 2d). The measured mass of this RNA is 388,270 Da, whereas the mass calculated from the gene sequence is 386,606 Da. Given that the sample most likely is a heterogeneous mixture of the species expected from the gene sequence with less abundant products extended by one to three extra nucleotides (Melton, D. A. et al., (1984) *Nucleic Acids Res.* 12: 7035–7056), the actual mass of the RNA sample is probably about 500 Da larger than the one calculated from the sequence. It would therefore appear as though a mass accuracy of at least about 1% as observed for DNA, can also be achieved for RNA.

For external 4 point calibrations of large DNA/RNA with molecular masses between 100–400 kDa, either clusters of cytochrome C (e.g. $10M^+$, $20M^+$, $30M^+$, $40M^+$) or multimers of an IgG monoclonal antibody (e.g. $2M^+3M^+$, $4M^+$) were used. For analytes exceeding 500 kDa the calibration with IgG monoclonal antibody was found to be most exact. Mass calibration of unknown DNA fragments using DNA or RNA calibrants may be more desirable, resulting in a more accurate mass determination.

Experiments to evaluate the sensitivity of IR-MALDI-MS of large nucleic acids with glycerol as matrix have been carried out with a PCR-product of approximately 515 nt and unknown sequence. Its mass was measured to 318,480 Da. For these measurements, glycerol, not subjected to ion exchange purification, was used. The spectra show dominant signals of the double stranded moiety. Tentatively the dissociation of the double strands in samples prepared with purified glycerol is attributed to an acidification of the glycerol by the protons exchanged for the cations. Although additional parameters may be involved in the double strand dissociation under IR-MALDI conditions. The starting concentration for the dilution experiment was 0.6 pmol/L as determined by UV spectrophotometry. The mass spectra in FIG. 3 were obtained by loading different amounts of sample onto the target. For the single shot mass spectrum in FIG. 3a, 300 fmol of the PCR-product had been loaded. The quality of this spectrum with an S/N-ratio better than 100 and a mass resolution of 65 (FWHM) for the double-strand indicates that the analyte to matrix ratio (A/M) of about $10^{-7}$ is well suited for an analyte of this size (about 320 kDa).

Figure 3B:
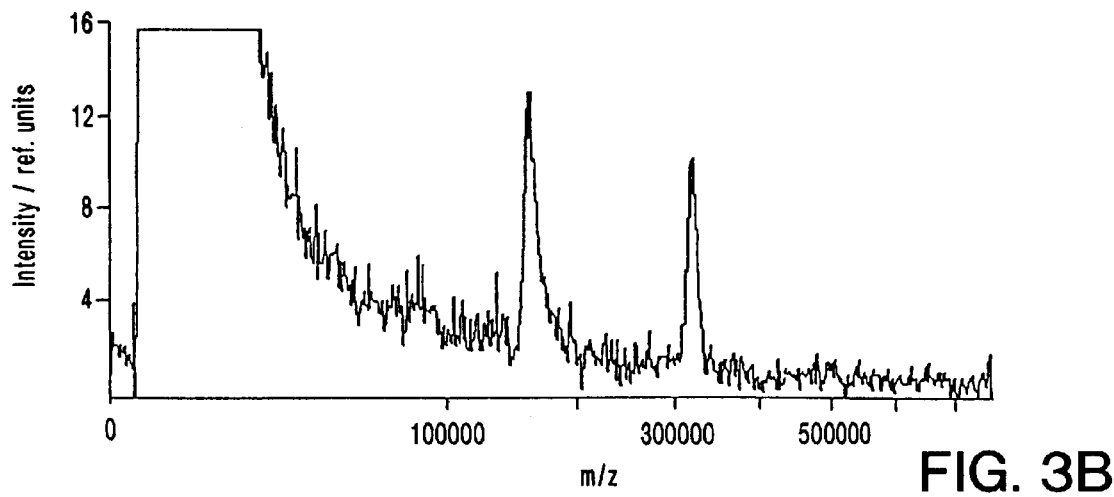
Figure 3C:
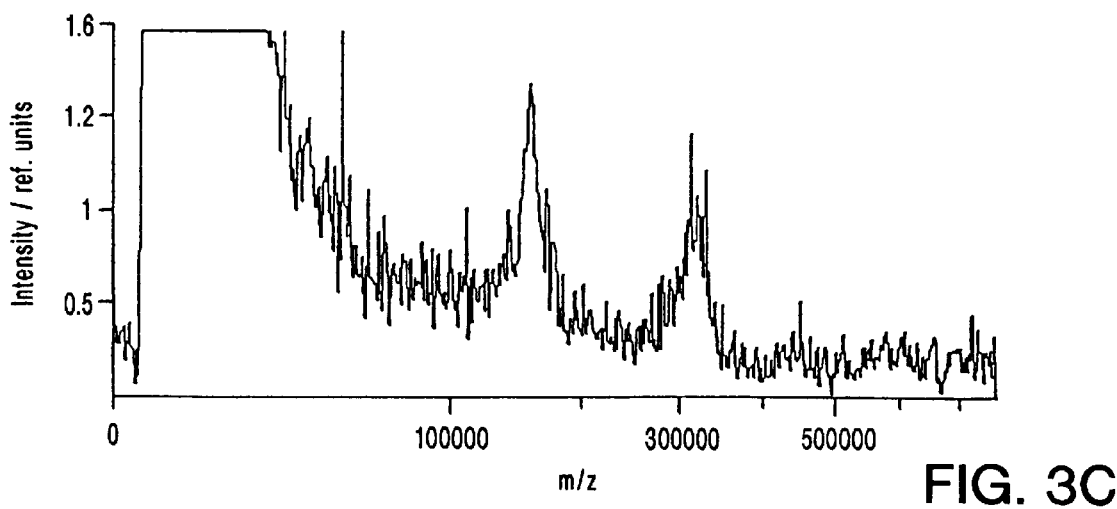

The mass spectrum in FIG. 3b was obtained using a 3 fmol total load (A/M about $2\times10^{-9}$). A strong background signal now dominates the low mass range. Total signal intensity, mass resolution (of about 25 FWHM for the ds-ion signal) and S/N-ratio are significantly degraded compared to FIG. 3a. However, mass determination is still possible with an accuracy of about 1%. The spectrum in FIG. 3c has been obtained from a very small sample volume forming an approximately 270 μm diameter sample spot on the target and a total sample load of only 300 amol (A/M about $8\times10^{-10}$). Such small sample volumes can be realized by either dispensing the small volumes by micropipettes as described in the literature (See e.g. Little, D. P., (1997) *Anal. Chem.* 69: 4540–4546) or by preparing the analyte in a standard microliter volume of a suitable glycerol/water mixture. In the latter case, the water is then evaporated off prior to or upon insertion of the sample into the vacuum. The poor mass resolution of only about 10 classifies this amount of analyte as the limit for the given instrument and detection system for a mass accuracy of better than about 3%. Compared to values reported for UV-MALDI-MS (Tang, K. et al., (1994) *Rapid Commun. Mass Spectrom.* 8: 727–730; and FIGS. 5 and 6), the sensitivity demonstrated here for IR-MALDI-MS demonstrates an improvement of at least about 2–3 orders of magnitude for nucleic acids of this size.

EXAMPLE 2
Performance of IR Matrix-Assisted Laser Desorption/Ionization Mass Spectrometry The performance characteristics of two lasers emitting in the mid infrared, an Er-YAG (2.94 μm wavelength, 80–90 ms pulse width), and an Er-YSGG infrared laser (2.79 μm wavelength, 80 ns pulse width), in matrix-assisted laser desorption/Iionization mass spectrometry (IR-MALDI-MS) of biological macromolecules, was studied. Glycerol and succinic acid were used as matrices. In IR-MALDI sample consumption per laser shot typically exceeds that of UV-MALDI by about two orders of magnitude. Using glycerol as matrix, the reproducibility of the ion signals from shot to shot is comparable to the best values achieved in UV-MALDI. The same holds true for the precision and accuracy of the mass determination. For succinic acid all these values are significantly worse, due to the strong sample heterogeneity as typically found in dried droplet preparations. Metastable fragmentation is comparable for UV- and IR-MALDI in the law mass range, but is significantly less for the IR in the mass range above ca. 20 kDA, leading to an improved mass resolution and an extended high mass limit for IR-MALDI.

In this Example (reproduced from Berkenkamp, S. et al., (1997) *Rapid Commun. Mass Spectrom.* 11:1399–1406 and incorporated by reference herein and in copending U.S. application Ser. No. 09/074,936), results and performance data for IR-MALDI analysis obtained with ER lasers emitting at 2.94 μm and 2.79 μm, and the applicability of delayed extraction for an improved mass resolution, is presented. In particular, is demonstrated that the extent of metastable fragmentation is different for the mass resolution of high molecular mass analytes.

Experimental

The experiments were carried out with an in-house built, single stage reflectron TOF mass spectrometer of 3.5 m equivalent flight length. The mass spectrometer can also be used in linear mode. Unless specifically mentioned, the experiments reported here have been carried out in reflectron mode. In the split extraction source, ions are accelerated through total potential differences of 12–20 kV using either static or delayed extraction. In the delayed mode extraction, a maximum potential difference of 8 kV can be switched; the minimum delay for ion extraction is 120 ns. No arcing was observed under these operation conditions in the positive or negative ion modes for any of the matrices used. A venetian blind secondary electron multiplier. (EMI R2362) with a conversion dynode, mounted 10 mm in front of the cathode (ion impact energy 20–27 kV, depending on ion mass), or a Chevron microchannel plat detector (Galileo Co., Sturbridge, Mass., USA), are used for ion detection. Signals were processed by a transient recorder with a time resolution of 2.5 ns (LeCroy 9450A) in the majority of the experiments. For the high mass-resolution experiments a LeCroy 9348La recorder with a time resolution of 0.5 ns was used. The data are transferred to a PC for storage and further evaluation. The instrument is equipped with two infrared lasers, one emitting at 2.94 $\mu$m (Er-YAG:Fa.Spectrum GmbH, Berlin, Germany: T=80–90 ns, energy stability ca. ±2–4% from shot to shot) and a second radiating at 2.79 $\mu$m (Er-YSGG: Schwartz Electro Optics. USA: T=80 ns; energy stability ca. ±2%). A frequency tripled Nd-YAG laser, emitting in the UV at 355 nm (T=16 ns) is used for direct comparison between IR- and UV-MALDI. Single laser-pulses are focused to a spot diameter of ca. 200 $\mu$m (IR) and 100 $\mu$m (UV) on the sample under an angle of 45°. Samples are observed in situ with a CCD camera of ca. 5 $\mu$m resolution. The stainless steel substrate can be cooled with liquid nitrogen to a temperature of ca. 150–170 K. Its temperature is monitored by a thermo-couple with an accuracy of ±5 K.

Sample Preparation

A wide variety of small molecules can be used as matrices in IR-MALDI as described previously. Succinic acid (solid matrix) and glycerol (fluid or frozen, solid) were preferred. DHBs (2,5-dihydroxybenzoic acid mixed with 10% 2-hydroxy-5-methoxybenzoic acid), a common matrix in UV-MALDI also functions in IR-MALDI and was used for comparison in some cases. Additionally, mixtures of compounds, e.g. succinic acid/DBHs or succinic acid/TRIS (Tris-hydroxymethylaminomethane) were found suitable. Solid matrix samples were prepared using the standard dried droplet method by mixing ca. 1–3 $\mu$l of a $10^{-4}$ $10^{-5}$ M aqueous analyte solution with 1–5 $\mu$L of a 30 g/L matrix solution on the target and subsequently drying in a stream of cool air.

For glycerol, analytes were either dissolved directly at a concentration of 0.5–10 g/L, or the glycerol was mixed with an aqueous analyte solution to a final analyte-to-glycerol molar ration of $2 \times 10^{-4}$–$1 \times 10^{-5}$, depending on the mass of the analyte. A volume of typically 1 $\mu$L is applied to the stainless steel substrate and smeared out evenly over an area of ca. 3–4 mm² to form a homogeneous, transparent thin layer. If an aqueous analyte solution is mixed with the glycerol, the water must be evaporated off before sample introduction into the mass spectrometer, usually at a pressure of $10^{-2-1}$ Pa. Samples are either inserted directly into the mass spectrometer or are cooled down to a temperature of ca. 150–170 K in liquid nitrogen before insertion.

For the matrices investigated, IR-MALDI was found to be quite tolerant with respect to salts and buffers. Spectra of samples containing NaCl at concentrations of up to 200 mM, saccharose up to 20% (w/v) or Tris/HCl buffer up to 100 mM have, for example, been obtained without significant loss in spectral quality with succinic acid as well as glycerol.

Results

Sample Consumption and Analytical Sensitivity

The analytical sensitivity of MALDI can be limited by either the minimal concentration of the analyte solution used for the analysis or the total amount of analyte available. For the actual measurement the total sample volume used for the preparation and the analyte-to-matrix ratio in the sample can be adjusted within certain limits to accommodate a given situation. In this section typical, as well as limiting, values for these quantities in IR-MALDI is presented and compared to the corresponding UV-MALDI values. As an introduction a few general differences between IR- and UV-MALDI will be discussed.

Given comparable laser spot sizes on the sample, 100–1000-times more material is desorbed by the IR as compared to the UV laser beam, because of the correspondingly smaller absorption coefficient and higher penetration depth of the radiation into the sample. Under the experimental conditions described here the single shot ion signals in the IR and UV typically were of comparable intensity. With that much more material ablated per laser pulse in IR-MALDI, the material is either primarily removed as larger clusters and small particles, as actually observed experimentally, and/or the ion yield is smaller by two to three orders of magnitude.

The intensity of low mass signals, the signal-to-noise ratio and mass resolution are the main criteria for the quality of recorded mass spectra. The optimal molar analyte-to-matrix ration on the target for the signal intensity and quality of spectra depends on the molecular mass of the analyte. For analytes with molecular masses below ca. 50 kDa a ratio of $2 \times 10^{-4}$–$2 \times 10^{-5}$ was found to be optimal. A ratio of $10^{-5}$ was found to work best for analytes with masses exceeding 50 kDa. Hence, in particular in the low mass range, the optimal analyte concentration in IR-MALDI exceeds that typically used in UV-MALDI by approximately one to two orders of magnitude. Spectra of reasonable quality can be obtained for analyte-to-matrix ratios down to $2 \times 10^{-6}$–$10^{-7}$, depending on molecular mass of the analyte. This corresponds to a sample consumption per laser shot of 1–50 fmol. In routine applications, spectra of IgG monoclonal antibodies (ca. 150 kDa) have been obtained with reasonable quality using $10^{-7}$ M aqueous solutions using either succinic acid or glycerol as matrix. This compares to values of only a few attomole in UV-MALDI.

The results demonstrated the attainable sensitivity for a lysozyme/glycerol preparation. Here, $5.5 \times 10^{-3}$ $\mu$L of a $1.2 \times 10^{-7}$ mol/L frozen glycerol solution, corresponding to a total amount of prepared lysozyme of ca. 0.7 fmol, were used for the preparation. This corresponds to a molar A/M-ratio of ca. $10^{-8}$. The frozen sample on the target had a diameter of about 1.5 times that of the laser spot on the sample. After the ten laser exposures summed for the spectrum some sample was still left on the target. Consequently, sample consumption of average was less than 70 attomol per single spectrum. However, when using such low A/M ratios the mass resolution is down at ml/$\Delta$m=10–20. The signal-to-noise (S/N) ratio has also degraded substantially and the low mass background signals become excessive. For UV-MALDI a sample consumption in the high zeptomole range has been reported (see, Jespersen et al. (1996) p. 217 in *Mass Spectrom. in Biol. Sci*, Burlingame, Ed.).

In IR-MALDI there is also a pronounced dependence on the A/M ratio of the yield of (non-specific) analyte oligomers or multiply charged ions. These tendencies are more pronounced in IR- as compared to UV-MALDI. A mass spectrum of hen egg lysozyme from a preparation with a A/M-ration of $2 \times 10^{-4}$ was obtained. Homo-oligomers of lysozyme up to the 25th mer (ca. 500 kDA) were identified in this spectrum. Conversely, signals of multiply charged analyte ions become dominant in the spectra for A/M-ratios below a value of ca. $10^{-6}$ whereas oligomer signals decrease to values below the noise level. These trends have also been observed with succinic acid and the water of hydration as matrices ( ) Sadeghi (1997) *Rapid Commun. Mass. Spectrom.* 11:393), and are particularly pronounced for analytes with molecular masses exceeding 50 kDa. Given the observed high yield of analyte homo-oligomers, the details of the distribution in particular the most abundant oligomer signal, can be influenced significantly by changes in the ion extraction conditions, e.g. by using low (soft or mild) or high (hard or harsh) ion extraction fields in a two stage ion source. Low extraction fields will shift the distribution towards a higher degree of oligomerization. This observation is a strong indication of gas phase processes in the expanding desorption plume besides possibly reflecting differences in the acceptance of the spectrometer under different extraction conditions.

Reproducibility

For Er-YAG lasers presently used, the pulse shot-to-shot stability is ca. ±2%, a value quite comparable to that of the best UV lasers, and, thus, does not contribute substantially to signal variation. Laser energy fluctuations from shot to shot, therefore, play only a minor role with these lasers. Another source of signal variation from shot-to-shot is the sample homogeneity, which depends on the matrix and the preparation technique. Solid matrices such as succinic acid typically form heterogeneous microcrystalline patterns. High quality mass spectra can only be achieved from 'sweet spots'. For some matrices like DHB (2,5-dihydroxybenzoic acid mixed with 10% 2-hydroxy-5-methoxybenzoic acid) this is also true for UV-MALDI. In UV-MALDI 50–100 spectra can be obtained from any 'sweet spot', in contrast to only 3–4 spectra from a given 'sweet spot' in IR-MALDI, because of the much larger sample consumption per exposure.

Liquid matrices such as glycerol form very homogeneous layers and spectra of comparable quality can be obtained from all locations across the sample. Also, the surface of these liquid samples recovers after every laser shot and more than 500 spectra of almost identical quality can be obtained from the same spot of a typical penetration. The spectrum of hen egg lysozyme was obtained after more that 250 shots on the same location at a laser repetition rate of 2 Hz. No significant differences in signal intensity, mass resolution, or S/N ratio as well as oligomer distribution, were observed between the early and late exposures. As a result, reproducibility of IR-MALDI spectra was found to be comparable to, if not better than, that for UV-MALDI preparations if glycerol is used as matrix. For solid matrices such as succinic acid reproducibility of ion signals from shot to shot may become a problem and considerable experience of the operator is often required for good results.

Fragmentation

Fragmentation is also an important parameter in MALDI-MS. Generally the yield of so call 'prompt' fragments, generated during the desorption and ionization process on a time scale short compared to the ion extraction time, is very low in UV-as well as IR-MALDI. These fragments are detected at their true (fragment) mass in linear as well as reflecting time-of-flight (TOF) spectrometers. This is also true under delayed extraction with delay times of ca. 1 $\mu$s or less. In IR-MALDI, a somewhat increased yield for such prompt fragments of oligonucleotides has been observed but the overall yield was very low nonetheless. Metastable ion decay, on the microsecond to hundreds of microseconds time scale in the field free region of the TOF mass spectrometer is much more important. On the one hand it degrades mass resolution in reflectron (reTOF) instruments, but on the other hand it can be used for structural analysis in the post-source decay (PSD) mode. No significant differences between UV- and IR-MALDI have so far been found for the metastable fragmentation of peptides and proteins in the mass range up to ca. 20 kDa. For analytes with a molecular mass above 20 kDa a markedly different metastable fragmentation has been observed. reTOF spectra of an IgG monoclonal antibody (mouse, MW ca. 150 kDa) obtained with UV-(matrix: DHBs) and IR-MALDI (matrix: succinic acid; matrix: glycerol) were obtained. The base peak of the parent ion had a rather symmetrical shape in both IR-MALDI spectra, whereas it showed a strong tail on the low mass side in the UV-MALDI spectrum, testifying to a significant amount of metastable decay. The peak width full width at half maximum (FWHM) decreases from a value of 2000 Da in the UV spectrum to values of 1000 Da in the IR spectrum with succinic acid as matrix, and merely 700 Da if glycerol is used as matrix. It was also noticeable that the analyte signals ride on a substantially elevated baseline in the UV-MALDI spectrum which results from delayed fragmentations somewhere within the ion source. No such baseline distortions were observed in the IR-MALDI spectra if the desorption fluence remained within a range of ca. 1–1.5 times ion detection threshold fluence.

It has been reported in the literature that in UV-MALDI the degree of metastable decay increases significantly with degrading source back pressure. Two spectra of an IgG monoclonal antibody (mouse) were obtained with (a) UV- and (b) IR-MALDI at a source back pressure of $4 \times 10^{-3}$ Pa as compared to a back pressure of $4 \times 10^{-4}$ Pa used to obtain the spectra described above. The UV-MALDI spectrum exhibited signals with a substantially increased tailing to the low mass side, particularly visible for the oligomers $2M^-$ and $3M^{2-}$; whereas no such tailing was seen in the IR-MALDI spectrum.

Another observation is the dependence of metastable fragmentation on the analyte-to-matrix ratio. In reTOF UV-MALDI, too high a A/M-ratio will usually result in a degraded S/N ratio and a loss of mass resolution. This was shown in with spectra for cytochrome c and DHB as the matrix. A higher A/M-ratio of $10^{-3}$ used to obtain the spectrum, resulted in a strong, low-mass tail of the peaks, again stronger for the dimer as compared to the parent ion peak, but not seen in the spectrum obtained from a sample with an A/M ratio of $10^{-4}$. The IR-MALDI spectrum shown of the same sample used showed no such tailing, again indicating substantially less metastable fragmentation. For IR-MALDI of cytochrome c using the water of hydration as 'intrinsic' matrix the molar A/M ratio is even higher (ca. $5 \times 10^{-3}$), yet no significant metastable decay was observed (Berkenkamp et al. (1996) *Proc. Natl. Acad. Sci. U.S.A.* 93:7003), It is a generally held notion that collisions of ions with matrix neutrals in the plume and with residual gas molecules in the spectrometer are the major cause of metastable fragmentation (see, e.g., Spengler et al. (1992) *J. Phys. Chem.* 96:9678). Considering that much more material is desorbed in IR versus UV-MALDI, resulting presumably in a more extended plume, and that in addition proportionally more of the absorbed laser energy goes into the analyte molecule in the IR, the finding of much less metastable fragmentation in IR-MALDI under all the different conditions presented above was not expected. Contrary to intuition, IR-MALDI seems to be a milder method than UV-MALDI.

Accessible Mass Range

The lower degree of fragmentation gives IR-MALDI an advantage over UV-MALDI for the analysis of very high mass analytes, particularly when an ion mirror is used. Not only does this lead to stronger signals of large parent molecular ions, it also, and more importantly, allows the use of higher laser fluences up to about twice the ion detection threshold fluence without deterioration in spectral quality as would be the case in UV-MALDI under such conditions. This increases the high mass signals even further.

A spectrum of gramicidin-S-synthetase of mass 510 kDa, prepared in glycerol matrix from an aqueous solution containing 50 mM Tris/HCL, 18% (w/v) saccharose and 5 mM dithiothreitol, with a quite acceptable S/N ratio and mass resolution of m/Δm=50 was obtained. No signals of this analyte could be obtained with UV-MALDI under a variety of conditions tried.

A mass spectrum of an IgG monoclonal antibody (mouse) demonstrated that IR-MALDI in combination with a TOF mass analyzer can be used for the analysis of biomolecules with molecular weights exceeding 1 MDa. Multiply charged ions of the 13-mer homo-oligomer of ca. 2 MDa mass could unambiguously be identified in the spectrum and signals of ions of other oligomers with m/z values as high as 900 000 were also clearly identified in the spectrum.

Mass Resolution

Delayed ion extraction (DE) is used for enhanced mass resolution in UV-MALDI-TOF MS. It was not immediately clear whether DE would be as advantageous in IR-MALDI as well, considering the much higher desorbed sample amount and the possibly substantially different plume expansion dynamics. In fact, for peptides in the 1000 Da mass range, the mass resolution is only about 200 (FWHM), down from about 1000 for UV-MALDI under otherwise comparable conditions, indicating difference in the ion generation process. Nonetheless DE gave equal mass resolution for IR- and UV-MALDI within the accuracy of the measurement. This was demonstrated with a reTOF spectrum (sodiated gramicidin-s, MW 1164.5 Da) obtained with the Er-YAG laser at 2.94 μm and 80 ns pulse width and succinic acid as matrix. The mass resolution in this spectrum was 1000, corresponding to a width of the individual peaks of 3.5 ns, limited by the time resolution of the dual MCP detector (3.0 ns). Using a reTOF for Mellitin (2846 Da) a mass resolution of 9500 and one of 1500 for cytochrome c (12360 Da) were obtained. Thus an enhancement in resolution by factors of ca. 50 for peptides and of 4 for cytochrome c was achieved.

In the high mass range mass resolution in the linear TOF with static ion extraction at 20 kV is limited to a value of ca. 50, equal for IR- and UV-MALDI. In both cases the mass resolution is determined by the distribution of initial ion velocities and kinetic energies. Using DE the mass resolution could be improved by a factor of 3 to equal values of ca. 150 for IR- as well as UV-MALDI.

For analytes exceeding 50 kDa mass resolution in IR-MALDI can, however, be improved even more with a reTOF analyser, in contrast to UV-MALDI. As demonstrated by the spectra discussed above (reTOF spectra of an IgG monoclonal antibody) the strongly decreased metasable fragmentation in IR-MALDI resulted in a peak width of only 700 Da for the parent ion peak of a monoclonal antibody desorbed with the IR-laser out of a glycerol matrix, compared to a peak width of ca. 2000 Da for the UV-MALDI spectrum. The peak width of 700 Da, corresponding to a resolution of about 200, was the best obtained for all experimental conditions tested. Using either a matrix other than glycerol, or an Er-YAG laser with a longer pulse width (≧120 ns instead of ≦90 ns) or switching to the Er-YSGG laser at a wavelength of 2.79 μm and 80 ns pulse width, led to slightly larger peak widths. No significant improvement in mass resolution was observed for the IR-MALDI reTOF spectra using DE for large masses, in agreement with observations made in UV-MALDI. Electrospray mass spectra of an IgG monoclonal antibody[10] show that the peak width of 700 Da reflects the peak envelope of the various glycosylation states of the molecule. The instrumental mass resolution has, therefore, been even somewhat higher. This assumption was supported by a spectrum of chondroitinase in which the peak of the singly charged dimer was observed at mass 224 kDa with a peak width of 700 Da, corresponding to a mass resolution of 300.

Mass Accuracy and Precision

Similar to the reproducibility of the intensity of ion signals in IR-MALDI, precision of the mass determination as given by the standard deviation of sequential measurements depends on the matrix (sample morphology) as well as on the shot-to-shot variation of the laser pulse energy.

For prompt ion extraction and solid matrices, such as succinic acid and dried droplet preparations, mass precision is typically 400–500 ppm for molecular weights up to 150 kDa. It is limited by the strong heterogeneity of the sample morphology and the need for a frequent change of the desorption location on the sample as described above. For prompt extraction and liquid matrices such as glycerol, forming very homogeneous layers, variations in total flight time resulting from variations of the laser pulse energy determines the precision of the mass determination. If, for example, the laser energy is raised intentionally from threshold ($I_o$) to 1.51 $I_o$, an increase in flight time of ca. 0.1% for cytochrome c (total flight time ca. 253 μs) was observed. Thus for glycerol the precision of mass determination depends on the stability of laser output energy. For IR lasers of current design with glycerol as matrix, a precision of the mass determination of 200–400 ppm can be achieved up to a mass of approximately 150 kDa. For analytes below 30 kDa this precision is lower by about one order of magnitude than the values typically obtained in prompt extraction UV-MALDI. In the high mass regime, precision in IR-MALDI was found to be better by at least a factor of 2, most likely due to the enhanced mass resolution of IR-MALDI in this mass range.

The mass accuracy for prompt extraction IR-MALDI was determined by external calibration with 3 well known standards. (Low mass range: angiotensin (human), mellitin, bovine insulin; high mass range: cytochrome c (horse heart), apo-myoglobin (horse), subtilisin Carlsberg (*bacillus subtilis*)). In the mass range up to 30 kDa, 5 sum spectra of 15 single shots each were used to obtain the calibration factors from the calibration spectrum and the mass of the 'unknown' in the second spectrum. For both matrices, succinic acid and glycerol, the absolute mass accuracy has been found to be $10^{2-5 \times 10^3}$ ppm depending on molecular mass. For proteins up to 40 kDa the mass accuracy of 100–500 ppm is in good agreement with the previously described numbers for UV-MALDI (static extraction).[20] For analytes exceeding 40 kDA accuracy is $1-5 \times 10^3$ ppm.

CONCLUSIONS

As judged by the lesser degree of metastable fragmentation compared to the UV, IR-MALDI appears to be the 'milder' of the two techniques for generating biomolecular ions. Glycerol or an equivalent material is the matrix of choice for many applications because of its superior reproducibility in comparison to solid matrices. Among the two lasers tested in this study, Er-YAG laser performs slightly better than Ef-YSGG laser for glycerol and substantially better for succinic acid as matrix. The lesser metastble fragmentation makes IR-MALDI also particularly well suited for the analysis of high mass analytes in the reTOF mode. Delayed ion extraction works well with IR-MALDI, with results comparable to UV-MALDI.

What is claimed is:

1. A method for detecting the presence or absence of a nucleic acid in a sample, comprising:
   (a) mixing the nucleic acid with a liquid matrix;
   (b) analyzing the mixture using infrared matrix-assisted laser desorption/ionization mass spectrometry;
   (c) detecting the nucleic acid by determining the mass of the nucleic acid by a mass spectrometric format for separation and detection of desorbed and ionized molecules,
   wherein:
      the nucleic acid is detected if present in the sample;
      the nucleic acid comprises at least 280 nucleotides; and
      the accuracy for determining the mass of the nucleic acid is within about 1%.

2. The method of claim 1, wherein the sample is a biological sample.

3. The method of claim 1, wherein the nucleic acid comprises at least 2000 nucleotides.

4. The method of claim 1, wherein the nucleic acid is DNA.

5. The method of claim 1, wherein the nucleic acid comprises at least 1200 nucleotides.

6. The method of claim 1, wherein the nucleic acid is RNA.

7. The method of claim 1, wherein the presence or absence of the nucleic acid is indicative of the presence or absence of a genetic disease.

8. The method of claim 1, wherein the presence or absence of the nucleic acid is indicative of the presence or absence of a birth defect.

9. The method of claim 1, wherein the presence or absence of the nucleic acid is indicative of the presence or absence of an infectious organism.

10. The method of claim 1, wherein the presence or absence of the nucleic acid is indicative of the identity of a subject.

11. The method of claim 1, wherein delayed ion extraction is used in the matrix-assisted laser desorption/ionization mass spectrometry.

12. The method of claim 1, wherein the matrix has at least one of the following properties: (1) is miscible with a nucleic acid compatible solvent (ii) is vacuum stable, and (iii) is of an appropriate viscosity to facilitate dispensing of micro- to nenoliter volumes of matrix alone or mixed with a nucleic acid compatible solvent.

13. The method of claim 1, wherein the matrix is selected from the group consisting of: an alcohol, a carboxylic acid, a primary or secondary amine, a primary or secondary amide, a nitrile, a hydrazine and a hydrazide.

14. The method of claim 13, wherein the matrix is a substituted or unsubstituted alcohol.

15. The method of claim 14, wherein the alcohol is selected from the group consisting of glycerol, 1,2- or 1,3-propane diol, 1,2-, 1,3- or 1,4-butane diol and triethanolamine.

16. The method of claim 14, wherein the matrix is glycerol.

17. The method of claim 1, wherein the nucleic acid/matrix mixture is deposited onto a substrate selected from the group consisting of beads, capillaries, flat supports, pins and wafers.

18. The method of claim 1, wherein the nucleic acid/matrix mixture is deposited onto a substrate comprising a material selected from the group consisting of steel, gold, silver, aluminum, copper or silicon.

19. The method of claim 1, wherein the nucleic acid/matrix mixture is deposited onto a substrate comprising a material selected from the group consisting of polyethylene, polyprdpylene, polyamide and polyvinylidenefluoride.

20. The method of claim 1, wherein the nucleic acid/matrix mixture is deposited onto fields of a chip array, arrays of pins or beads in pits of flat surfaces.

21. The method of claim 1, wherein the sample is cooled to a temperature below about 20° C.

22. A method for detecting the presence or absence of a nucleic acid in a sample, comprising:

(a) mixing the nucleic acid with a matrix which forms a homogeneous solution with the nucleic acid;

(b) analyzing the mixture using infrared matrix-assisted laser desorption/ionization mass spectrometry; and (c) detecting the nucleic acid by determining the mass of the nucleic acid by a mass spectrometric format for separation and detection of desorbed and ionized molecules, wherein:

the nucleic acid is detected if present in the sample;

the nucleic acid comprises at least 280 nucleotides; and the accuracy for determining the mass of the nucleic acid is within about 1%.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:1:

CGCCTGAGTA GTACGTTCGC                                                   20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:2:

GCGGTGTGTA CAAGACCCGA                                                   20